US010578624B2

(12) United States Patent
Naimy et al.

(10) Patent No.: US 10,578,624 B2
(45) Date of Patent: Mar. 3, 2020

(54) DETERMINATION OF GLYCOSAMINOGLYCAN LEVELS BY MASS SPECTROMETRY

(71) Applicant: Shire Human Genetic Therapies, Inc., Lexington, MA (US)

(72) Inventors: Hicham Naimy, Lexington, MA (US); Yongchang Qiu, Lexington, MA (US); Patrick Anthony John Haslett, Somerville, MA (US); Ann Barbier, Lexington, MA (US)

(73) Assignee: Shire Human Genetic Therapies, Inc., Lexington, MA (US)

(*) Notice: Subject to any disclaimer, the term of this patent is extended or adjusted under 35 U.S.C. 154(b) by 38 days.

(21) Appl. No.: 15/526,217

(22) PCT Filed: Nov. 13, 2015

(86) PCT No.: PCT/US2015/060714
§ 371 (c)(1),
(2) Date: May 11, 2017

(87) PCT Pub. No.: WO2016/077775
PCT Pub. Date: May 19, 2016

(65) Prior Publication Data
US 2017/0350900 A1 Dec. 7, 2017

Related U.S. Application Data

(60) Provisional application No. 62/080,154, filed on Nov. 14, 2014.

(51) Int. Cl.
*G01N 33/68* (2006.01)
*G01N 33/48* (2006.01)
*C12Q 1/34* (2006.01)

(52) U.S. Cl.
CPC .......... *G01N 33/6848* (2013.01); *C12Q 1/34* (2013.01); *G01N 33/6893* (2013.01); *G01N 2400/40* (2013.01); *G01N 2560/00* (2013.01); *G01N 2800/042* (2013.01); *G01N 2800/52* (2013.01)

(58) Field of Classification Search
CPC .............. C12Q 1/34; G01N 2560/00; G01N 2800/042; G01N 2800/52; G01N 33/48; G01N 33/6848; G01N 33/6893; G01N 2400/40; Y10T 436/143333; Y10T 436/17; Y10T 436/173845; Y10T 436/203332; Y10T 436/24
USPC ........... 436/63, 94, 106, 111, 131, 161, 173; 422/70; 435/18
See application file for complete search history.

(56) References Cited

U.S. PATENT DOCUMENTS

| | | | |
|---|---|---|---|
| 2006/0286034 A1* | 12/2006 | Meikle | G01N 33/66 424/9.2 |
| 2007/0161074 A1 | 7/2007 | Tomatsu et al. | |
| 2010/0184013 A1* | 7/2010 | Crawford | G01N 33/66 435/4 |

FOREIGN PATENT DOCUMENTS

| | | |
|---|---|---|
| CN | 103713057 A | 4/2014 |
| WO | WO2011/163649 A2 | 12/2011 |

OTHER PUBLICATIONS

Volpi, Nicola. Analytical Biochemistry, vol. 397, Sep. 19, 2009, pp. 12-23.*
Sakai et al. Analytical Biochemistry, vol. 302, Feb. 13, 2002, pp. 169-174.*
Ramsay et al. Molecular Genetics and Metabolism, vol. 78, 2003, pp. 193-204.*
Muenzer et al., "Long-term, Open-labeled Extension Study of Indursulfase in the Treatment of Hunter Syndrome", Genetics in Medicine, 13(2) 95-101 (2011).
Burton, B. K. et al., "Diagnosing Hunter syndrome in pediatric practice: practical considerations and common pitfalls" Eur. J. Pediatr, 171(4): 631-639 (2012).
Galeotti, F. et al., "Online Reverse Phase-High-Performance Liquid Chromatography-Fluorescence Detection-Electrospray Ionization-Mass Spectrometry Separation and Characterization of Heparan Sulfate, Heparin, and Low-Molecular Weight-Heparin Disaccharides Derivatized with 2-Aminoacridone", Anal. Chem., 83(17): 6770-6777 (2011).
Gill, V. L. et al., "Disaccharide Analysis of Glycosaminoglycans Using Hydrophilic Interaction Chromatography and Mass Spectrometry", Anal. Chem., 85(2): 1138-1145 (2013).
Hitchcock, A. M. et al., "Improved workup for glycosaminoglycan disaccharide analysis using CE with LIF detection", Electrophoresis, DE, 29(22): 4538-4548 (2008).
Holt, J. et al., "Early Clinical Markers of Central Nervous System Involvement in Mucopolysaccharidosis Type II" J. Pediatr., 159(2): 320-326 (2011).
Martin, R. et al, "Recognition and Diagnosis of Mucopolysaccharidosis II (Hunter Syndrome)", Pediatrics, 121(2): E377-E386 (2008).
Muenzer, J. et al., "Multidisciplinary Management of Hunter Syndrome", Pediatrics, 124(6): E1228-E1239 (2009).

(Continued)

*Primary Examiner* — Maureen Wallenhorst
(74) *Attorney, Agent, or Firm* — Proskauer Rose LLP; Fangli Chen; Julio J. Mendez

(57) ABSTRACT

Detecting glycosaminoglycans (GAGs) and/or determining the level of one or more glycosaminoglycans can be useful, e.g., in identifying or monitoring various medical conditions, the status of patients having various medical conditions, and/or the response to treatment of individuals having various medical conditions. The present invention provides methods for detecting glycosaminoglycans and/or determining the level of glycosaminoglycans through the use of, e.g., mass spectrometry.

11 Claims, 11 Drawing Sheets

(56) References Cited

OTHER PUBLICATIONS

Pabst, M. et al., "Comparison of fluorescent labels for oligosaccharides and introduction of a new postlabeling purification method", Anal. Biochem., 384: 263-273 (2009).
Scarpa, M. et al., "Mucopolysaccharidosis type II: European recommendations for the diagnosis and multidisciplinary management of a rare disease", Orphanet J. Rare Dis., 6(1): p. 72 (2011).
Vedolin, L. et al., "Brain MRI in mucopolysaccharidosis", Neurology, 69(9): 917-924 (2007).

* cited by examiner

| DISACCHARIDE | R1 | R2 | R3 |
|---|---|---|---|
| IS | $SO_3H$ | $SO_3H$ | $SO_3H$ |
| IIS | $SO_3H$ | $SO_3H$ | H |
| IIIS | $SO_3H$ | H | $SO_3H$ |
| IVS | $SO_3H$ | H | H |
| IA | Ac | $SO_3H$ | $SO_3H$ |
| IIA | Ac | $SO_3H$ | H |
| IIIA | Ac | H | $SO_3H$ |
| IVA | Ac | H | H |

DETERMINATION OF GLYCOSAMINOGLYCAN LEVELS BY MASS SPECTROMETRY

CROSS-REFERENCE TO RELATED APPLICATIONS

This application is a U.S. National Stage Application filed under 35 U.S.C. § 371, based on International Application No. PCT/US2015/060714, filed Nov. 13, 2015, which claims priority to U.S. Provisional Application No. 62/080,154, filed Nov. 14, 2014, the disclosure of which is hereby incorporated by reference in its entirety.

BACKGROUND

Various medical conditions are associated with the accumulation of glycosaminoglycans. Glycosaminoglycans (GAGs) are large complex carbohydrate molecules that participate in many biological processes. Glycosaminoglycans include polysaccharides derived from amino hexose, such as heparan, heparan sulfate (HS), hyaluronic acid, keratan sulfate, chondroitin sulfate, dermatan sulfate, and copolymers thereof. Various GAGs differ according, e.g., to the type of hexosamine, hexose, or hexuronic acid unit that they contain, as well as in the geometry of the glycosidic linkage between these units. In some instances, a GAG molecule can be broken down into disaccharide components. GAGs and GAG-derived disaccharide components can exhibit a great deal of structural heterogeneity with regards to the extent of sulfation, acetylation, epimerization, and other characteristics. On account of, in part, such variations, GAGs encompass a broad array of distinct molecules, leading to variation that contributes to challenges in quantification and characterization.

Certain GAGs, e.g., HS, are not a single compound but rather a collection of related molecules with, in some instances, different molecular weights. This is one reason that quantification or characterization of such GAGs, including HS, is not readily achievable. There is a need in the art for additional and improved methods of determining GAG levels.

SUMMARY

Detecting glycosaminoglycans (GAGs) and/or determining the level of one or more glycosaminoglycans can be useful, e.g., in identifying or monitoring various medical conditions, the status of patients having various medical conditions, and/or the response to treatment of individuals having various medical conditions. The present invention provides methods for detecting glycosaminoglycans and/or determining the level of glycosaminoglycans through the use of, e.g., mass spectrometry. Such methods, uses thereof, apparatuses for their application, and related methods and compositions are further described herein. The methods described herein are improved over certain previous methods at least with respect to precision, accuracy, reproducibility, and throughput. In particular instances, one or more methods described herein are improved over certain previous methods at least with respect to precision. In other instances, the utility of certain embodiments of the present invention is instead or additionally the result of their applicability in identifying or monitoring various medical conditions, the status of patients having various medical conditions, and/or the response to treatment of individuals having various medical conditions.

Certain methods of the present invention, in order to circumvent certain challenges in GAG quantification, include the cleavage of one or more GAG molecules into disaccharide components with subsequent quantification of the GAG cleavage product disaccharides, such that the measured level of one or more GAG cleavage product disaccharides provides a surrogate for or alternative to direct quantification of one or more GAGs.

In certain instances in which a disaccharide is referred to in the singular (e.g., a "disaccharide" or an "individual disaccharide"), the term "disaccharide" can refer collectively to all molecules of a particular type that are present in a sample, population, or the like, regardless of whether or not reference is made a specific disaccharide.

As taught by the present disclosure, many GAG-derived disaccharides (e.g., GAG cleavage products), including certain isomeric dissacharides, can be resolved by reversed-phase (RP) chromatography, e.g., after their derivatization with a label, e.g., a hydrophobic label, e.g., 4-Butylaniline (4-NBA). In various embodiments the label contributes to separation of individual molecules or types of molecules during chromatography. The availability of an isotopically labeled internal standard ($I_{std}$) for one or more selected disaccharides can be included as a mechanism capable of conferring a high level of accuracy and reproducibility.

In at least one aspect, the present invention includes a method of determining glycosaminoglycan (GAG) level in a biological sample, the method including the steps of incubating a biological sample with one or more enzymes under conditions that permit digestion of glycosaminoglycan to generate a mixture of disaccharides; chemically derivatizing the mixture of disaccharides generated in the incubating step; measuring the amount of each individual derivatized disaccharide; and determining the glycosaminoglycan (GAG) level in the biological sample based on the amount of each individual derivatized disaccharide measured at the measuring step. In certain embodiments of such methods, the glycosaminoglycan includes heparan sulfate. In certain embodiments of such methods, including embodiments in which the glycosaminoglycan includes heparan sulfate, the one or more enzymes include one or more heparinases, e.g., heparinases I, II and/or III. In certain embodiments of such methods, including embodiments in which the glycosaminoglycan includes heparan sulfate, the one or more enzymes include one or more enzymes selected from the group consisting of chondroitinase AC, chondroitinase B, chondroitinase C, Chondroitinase ABC and keratanases.

In various methods of the present invention, such as those described above, the mixture of disaccharides can include disaccharides I-S (ΔUA,2S-GlcNS,6S), II-S (ΔUA-GlcNS,6S), III-S (ΔUA,2S-GlcNS), IV-S (ΔUA-GlcNS), II-A (ΔUA-GlcNAc,6S), and/or IV-A (ΔUA-GlcNAc).

In certain embodiments of the present invention, the measuring includes measuring the amount of each of derivatized I-S (ΔUA,2S-GlcNS,6S), derivatized II-S (ΔUA-GlcNS,6S), derivatized III-S (ΔUA,2S-GlcNS), derivatized IV-S (ΔUA-GlcNS), derivatized II-A (ΔUA-GlcNAc,6S), and derivatized IV-A (ΔUA-GlcNAc).

In various methods of the present invention, such as those described above, the mixture of disaccharides can be derivatized with a hydrophobic moiety.

In various methods of the present invention, such as those described above, the mixture of disaccharides are derivatized with 4-Butylaniline, 2-aminobenzamide (2-AB), 2 aminobenzoic acid (anthranilic acid; 2-AA), or 2-Aminoacridone (AMAC).

In various methods of the present invention, such as those described above, the measuring step can include, first, separating individual derivatized disaccharide by chromatography and, second, measuring each individual derivatized disaccharide by mass spectrometry. In particular embodiments, the chromatography is reverse-phase liquid chromatography In various methods of the present invention, such as those described above, the amount of each individual derivatized disaccharide is measured as compared to an internal standard. For instance, in particular embodiments, each individual disaccharide is derivatized with 4-Butylaniline and the internal standard for each corresponding disaccharide is labeled with $^{13}C_6$-4-Butylaniline.

In various methods of the present invention, such as those described above, the glycosaminoglycan (GAG) level in the biological sample is determined by summed disaccharide concentration value based on the amount of each individual disaccharide measured.

In various methods of the present invention, such as those described above, the biological sample is a cerebrospinal fluid (CSF) sample. In particular embodiments, the CSF sample has a volume ranging from about 10 μl to 100 μl (e.g., 10 μl to 100 μl, 10 μl to 75 μl, 10 μl to 50 μl, 25 μl to 100 μl, 25 μl to 75 μl, or 50 μl to 100 μl). In particular embodiments, the CSF sample has a volume ranging from about 45 μl to 55 μl.

In various methods of the present invention, such as those described above, the biological sample is a blood sample, a plasma sample, a urine sample, or a plasma sample or urine sample.

In various methods of the present invention, such as those described above, the biological sample is first processed to extract glycosaminoglycan.

In various methods of the present invention, such as those described above, the biological sample contains glycosaminoglycan-derived disaccharides at a concentration greater than 0.1 μM (e.g., greater than 0.1 μM, greater than 0.5 μM, greater than 1 μM, greater than 5 μM, or greater than 10 μM.

In at least another aspect of the present invention, the present invention includes a method of treating a lysosomal storage disease that includes treating a subject suffering from a lysosomal storage disease with a treatment course including administering to the subject a therapeutically effective dose of a replacement enzyme at an administration interval; measuring glycosaminoglycan (GAG) level in a biological sample obtained from the subject during the treatment course by a method of any one of the preceding claims; and maintaining the therapeutically effective dose and the administration interval if the glycosaminoglycan level is reduced by 10% as compared to a baseline GAG level prior to the treatment. In related embodiments, the therapeutically effective dose and the administration interval are maintained if the glycosaminoglycan level is reduced by, e.g., 1%, 2%, 3%, 4%, 5%, 10%, 15%, 20%, 25%, 30%, 40%, 50%, 60%, 70%, 80%, 85%, 90%, 91%, 92%, 93%, 94%, 95%, 96%, 97%, 98%, 99%, or even 100%. In related embodiments, the therapeutically effective dose and the administration interval are maintained if the glycosaminoglycan level is reduced by, e.g., at least 1%, at least 2%, at least 3%, at least 4%, at least 5%, at least 10%, at least 15%, at least 20%, at least 25%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99%. In related embodiments, the therapeutically effective dose and the administration interval are maintained if the glycosaminoglycan level is reduced by, e.g., to a normal or substantially normal level, to a control level, to within an experimentally or canonically defined normal range, to within a control range, or to a level that is within 1%, 2%, 3%, 4%, 5%, 10%, 15%, 20%, 25%, 30%, 40%, 50%, 60%, 70%, 80%, 85%, 90%, 91%, 92%, 93%, 94%, 95%, 96%, 97%, 98%, 99%, or 100% of any such level or any such range.

In at least another aspect of the present invention, the present invention includes a method of treating Hunter syndrome, including administering intrathecally to a subject in need of treatment a therapeutically effective dose of a recombinant iduronate-2-sulfatase (I2S) periodically such that glycosaminoglycan (GAG) level in cerebrospinal fluid (CSF) is reduced by more than 85% as compared to the baseline GAG level prior to the treatment, determined by a method of any one of the preceding claims.

In some embodiments, the present invention includes a method of treating SanA syndrome, including administering intrathecally to a subject in need of treatment a therapeutically effective dose of a recombinant heparan N-sulfatase periodically such that glycosaminoglycan (GAG) level in cerebrospinal fluid (CSF) is reduced by more than 10% as compared to the baseline GAG level prior to the treatment, determined by a method of any one of the preceding claims.

In at least one aspect, the present invention includes a method of monitoring treatment of a lysosomal storage disease, the method including treating a subject suffering from a lysosomal storage disease with a treatment course including administering to the subject a therapeutically effective dose of a replacement enzyme at an administration interval and measuring glycosaminoglycan (GAG) level in a biological sample obtained from the subject during the treatment course by any method thereof, e.g., a method of measuring GAG level as described herein. In certain embodiments, the lysosomal storage disease can be selected from the group consisting of MPSI, MPSII, MPSIIIA, MPSIIIB, MPSIIIC, MPSIIID, MPSIVA, MPSIVB, MPSVI, MPSVII, MPSIX, alpha mannosidosis, aspartylglucosaminuria, Fabry, fucosidosis, galactosialidosis, Gaucher disease, GM1 gangliosidosis, GM2 activator deficiency, sialidosis, Krabbe, metchromatic leukodystrophy, mucolipidosis IV, multiple sulfatase deficiency, Pompe, Sandhoff, Tay-Sachs, AB Variant Schindler Disease, Salla Disease, beta mannosidosis, and globoid cell leukodystrophy. In particular embodiments, the administering can be intrathecal administration or intravenous administration. In some embodiments, the dose can be selected from the group consisting of 10 mg, 45 mg, 90 mg and combinations thereof. In some instances, the replacement enzyme can be recombinant human heparan N-sulfatase or recombinant idursulfase. In various embodiments, the administration interval can be daily, weekly, biweekly, monthly, bimonthly, yearly or combinations thereof. In some methods as described herein, the biological sample can be selected from the group consisting of cerebrospinal fluid (CSF), whole blood, cells, tissue, plasma, serum, blood, urine and combinations thereof.

Certain methods as described herein can further include maintaining the therapeutically effective dose and/or the administration interval if the GAG level is or has been reduced as compared to a control GAG level, e.g., where the GAG level is or has been reduced by at least 10%, at least 20%, at least 30%, at least 40%, at least 50%, at least 60%, at least 70%, at least 80%, at least 90%, or more.

Certain methods as described herein can further include adjusting the therapeutically effective dose and/or administration interval if the GAG level is or has been reduced as compared to a control GAG level, e.g., where the adjusting the therapeutically effective dose and administration level can include increasing the dose and/or decreasing the administration interval. In some instances, the GAG level is or has been reduced by 1% or less, 2% or less, 3% or less, 4% or less, 5% or less, 6% or less, 7% or less, 8% or less, 9% or less or 10% or less.

Certain methods as described herein can further include adjusting the therapeutically effective dose and/or administration interval if the GAG level is or has been increased as compared to a control GAG level, e.g., where the adjusting the therapeutically effective dose and administration level can include increasing the dose and/or decreasing the administration interval. In some instances, the GAG level is or has been increased by at least 1%, at least 10%, at least 20%, at least 30%, at least 40%, at least 50%, at least 60%, at least 70%, at least 80%, at least 90% or more.

In various methods of the present invention, the control GAG level can be i) a GAG level in the subject suffering from the lysosomal storage disease, ii) a GAG level in the subject suffering from the lysosomal storage disease measured at an earlier time point during treatment, or iii) a GAG level in an untreated control subject.

In at least one aspect, the present invention includes a method of treating Hunter syndrome, including administering intrathecally to a subject in need of treatment a therapeutically effective dose of a recombinant iduronate-2-sulfatase (I2S) periodically such that glycosaminoglycan (GAG) level in cerebrospinal fluid (CSF) can be reduced by more than 85% as compared to the baseline GAG level prior to the treatment, determined by any method of determining the GAG level, e.g., any method as described herein.

Definitions

In order for the present invention to be more readily understood, certain terms are first defined. Additional definitions for the following terms and other terms are set forth throughout the specification. Insofar as the definitions do not conflict with the understanding of these terms by those of skill in the art, the definitions are not intended to exclude the common meaning of these terms.

Biomarker: As defined herein, the term "biomarker" refers to a substance (e.g., protein or nucleic acid) that can be used as an indicator of a disease, risk of developing the disease, carrier status, or responses to a therapeutic intervention. Typically, a suitable biomarker has a characteristic that can be objectively measured and evaluated as an indicator. In some embodiments, a biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney, odds ratio, Linear Discriminant Analysis, Quadratic Discriminant Analysis and K-nearest neighbor. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

Control: As used herein, the term "control" has its art-understood meaning of being a standard against which results are compared. Typically, controls are used to augment integrity in experiments by isolating variables in order to make a conclusion about such variables.

Derivatization: As used herein, "derivatizion" means to combine a first compound or molecule and a second actively provided compound or molecule by contacting the first compound or molecule with the second compound or molecule under conditions capable of allowing the first and second molecules or compounds to bind, e.g., in a stable or semi-stable manner. A derivatized sample, as used herein, means a sample having been subjected to a derivatization step. Accordingly, a "derivatized" compound or molecule as used herein is a compound or molecule having bound with a provided second compound or molecule. Where a particular second compound or molecule is expressly provided with respect to one or more particular embodiments, those of skill in the art will appreciate that a derivatized compound or molecule as used in such embodiments, except as otherwise provided, will refer to a compound or molecule having been bound with the provided second compound or molecule.

Digest: As used herein, "digest" means to disrupt one or more chemical interactions by which two or more component parts of a compound or molecule are joined, the disruption resulting in the separation of two or more of the two or more component parts. Digestion includes, e.g., enzymatic digestion of a compound or molecule by contacting the compound or molecule with an enzyme capable of cleaving the compound or molecule.

Effective amount: As used herein, the term "effective amount" refers to an amount of a compound or agent that is sufficient to fulfill its intended purpose(s). In the context of the present invention, the purpose(s) may be, for example: to modulate the expression of at least one inventive biomarker; and/or to delay or prevent the onset of GAG condition; and/or to slow down or stop the progression, aggravation, or deterioration of the symptoms of a GAG condition; and/or to alleviate one or more symptoms associated with a GAG condition; and/or to bring about amelioration of the symptoms of a GAG condition, and/or to cure a GAG condition.

Enzyme: As used herein, the term "enzyme" refers to any protein capable of producing changes in a biological substance by catalytic action.

Enzyme activity: As used herein, the term "enzyme activity", "enzymatic activity" or grammatical equivalent, refers to the general catalytic properties of an enzyme.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. In some embodiments, isolation involves or requires disruption of covalent bonds (e.g., to isolate a polypeptide domain from a longer polypeptide and/or to isolate a nucleotide sequence element from a longer oligonucleotide or nucleic acid).

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Level: As used herein, the term "level" means the absolute or relative amount, concentration, frequency, or qualitative of quantitative measure or expression thereof of a measurable quality or entity, e.g., a molecule, compound, type of molecule or compound, group of molecules or compounds, phenotype, genotype, symptom, event, or other measurable quality or entity.

Normal: As used herein, the term "normal," when used to modify the term "individual" or "subject" they refer to an individual or group of individuals who does not have a particular disease or condition and is also not a carrier of the disease or condition. The term "normal" is also used herein to qualify a biological specimen or sample isolated from a normal or wild-type individual or subject, for example, a "normal biological sample."

Sample: As used herein, the term "sample" means a small part of something intended to show the quality, nature or quantity of the thing from which it was derived. The term sample encompasses any sample obtained from any source.

Treatment: As used herein, the term "treatment" (also "treat" or "treating"), in its broadest sense, refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Sanfilippo syndrome, Hunter syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as having relevant disease, disorder, and/or condition. In some embodiments, treatment may be of a subject known to have one or more susceptibility factors that are statistically correlated with increased risk of development of relevant disease, disorder, and/or condition.

BRIEF DESCRIPTION OF DRAWINGS

FIG. 2A is a diagram depicting the chemical structure of 4-NBA and its $^{13}$C isotopically labeled version used in generating internal disaccharide standards. FIG. 2B is a diagram and graph depicting the reducing end of the disaccharide exists in equilibrium between a hydroxyl and an aldehyde group. During reductive amination, the primary amine of 4-NBA readily reacts with the aldehyde to form a covalent imine bond. The imine bond was further reduced with a reducing agents to make a more stable amine linkage. The high resolution mass spectrum showed a singly charged representative disaccharide (IIS) along with its internal standard that was 6 Da heavier.

DETAILED DESCRIPTION

Figure 1:
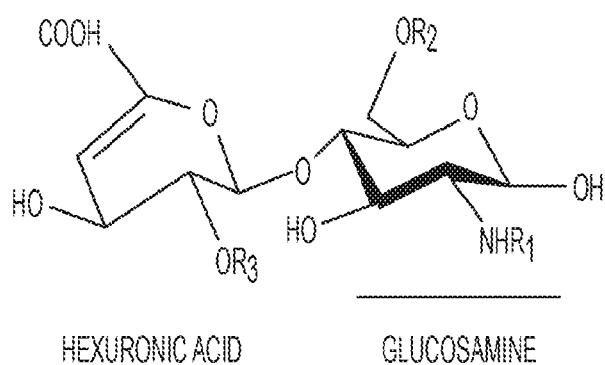
FIG. 1 is an exemplary diagram and table depicting Δ-unsaturated HS disaccharides generated by enzymatic depolymerization using heparinases. The general structure of HS disaccharides. The disaccharide contains a hexuronic acid linked to a glucosamine through an α/β 1-4 glycosidic linkage. The 4-5 Δ-unsaturation on the hexuronic acid is not a native feature but is introduced due the eliminative mechanism of the enzyme. Common sites of substitutions are shown: R1, R2 and R3. The disaccharides are structurally divided in two categories based on their N-substitution namely, N-sulfated and N-acetylated. In each category, disaccharides can be sulfated at different hydroxyl oxygens. Note that IIS/IIIS and IIA/IIIA are positional isomers with respect the O-sulfate positions

The present invention includes methods and compositions for determining the level of one or more glycosaminoglycans (GAGs). Certain GAGs, e.g., heparan sulfate (HS), are not a single compound but rather a collection of related molecules (HS GAG molecules) with, in some instances, different molecular weights. In various embodiments, the method can include steps of enzymatically digesting a biological sample (e.g., a biological sample that includes GAGs) to produce a digested biological sample and subsequently derivatizing the digested biological sample. Following derivatization, the sample can be analyzed to identify compounds present in the derivatized sample, where the identified compounds provide, directly or indirectly, the level of one or more glycosaminoglycans. Accordingly, in various embodiments, the invention is a method of determining the level of one or more GAGs (e.g., HS) in a sample, the method including steps of digesting, derivatizing, and analyzing.

In various embodiments of the present invention, analyzing includes one or more separation steps and one or more detecting steps. In general, separation can include separation by a technique such as chromatography or related methods known in the art. In general, detecting can include techniques such as mass spectrometry. Accordingly, in some particular embodiments, the invention includes a method of determining the level of one or more GAGs in a sample, the method including steps of digesting, derivatizing, separating, and detecting.

In various embodiments of the present invention, a biological sample is prepared for enzymatic digestion by a process of extraction. In various embodiments of the present invention, a biological sample is prepared (e.g., prepared for enzymatic digestion, derivatization, digestion followed by derivatization, or derivatization followed by digestion) by a process of extraction. In various embodiments of the present invention, a biological sample is prepared (e.g., prepared for enzymatic digestion, derivatization, digestion followed by derivatization, or derivatization followed by digestion) by a process of extraction followed by desalting. For instance, a clinical sample may be collected from one or more patients, and GAG can be extracted from the clinical sample. In some instances, the product produced by such extraction is desalted. Accordingly, in some particular embodiments, the invention includes a method of determining the level of one or more GAGs (e.g., HS) in a sample, the method including steps of extracting, digesting, derivatizing, separating, and detecting. Further, in some particular embodiments, the invention includes a method of determining the level of one or more GAGs in a sample, the method including steps of extracting, desalting, digesting, derivatizing, separating, and detecting. Any of two or more of these steps may be performed in any sequence, including particular embodiments including any of two or more of these steps in which the combination includes a terminal analyzing step insofar as the analyzing step is not necessarily followed by a further step selected from these steps, or particularly a terminal detecting step insofar as the detecting step is not necessarily followed by a further step selected from these steps.

In various embodiments, a method of the present invention can be utilized to monitor the progress of a disease or condition by monitoring the level of one or more GAGs (e.g., HS) or one or more components thereof. In certain embodiments, a method of the present invention can be utilized to monitor the level of one or more glycosaminoglycans or one or more components thereof in a subject, e.g., a subject having been treated with a therapeutic agent. In certain embodiments, a method of the present invention can be utilized to monitor the level of one or more glycosaminoglycans or one or more components thereof in a subject having been diagnosed as having or at risk of having a condition associated with a clinically significant modulation or imbalance of the level of one or more GAGs or one or more components thereof (a GAG condition). GAG conditions include, for example, MPSI, MPSII, MPSIIIA, MPSIIIB, MPSIIIC, MPSIIID, MPSIVA, MPSIVB, MPSVI, MPSVII and MPSIX (inclusive of, e.g., SanA and SanB), as well as Hunter Syndrome. In certain embodiments, a method of the present invention can be utilized to monitor the level of one or more glycosaminoglycans or a component thereof (e.g., a component disaccharide) in a subject having been diagnosed as having or at risk of having a lysosomal storage disorder or a GAG condition that is a lysosomal storage disorder.

In some embodiments, a method of the present invention is utilized in determining the level of one or more glycosaminoglycans or one or more components thereof in a subject having a medical condition associated with glycosaminoglycan imbalance. In certain embodiments, a method of the present invention is used in conjunction with a further metric or biomarker, e.g., a biomarker of a GAG condition, e.g., a qualitative or quantitative biomarker of the presence, activity, or progression of a GAG condition.

In various embodiments, a method of the present invention is utilized in determining the level of one or more glycosaminoglycans or one or more components thereof in an individual having been treated for a condition, e.g., a GAG condition.

In some embodiments, a method of the present invention is used to diagnose a condition associated with an imbalance in the level of one or more glycosaminoglycans relative to an absolute or relative standard, such as the level of one or more other glycosaminoglycans or other biomarker or biological molecule.

Various embodiments of the methods and compositions of the present invention are described in greater detail herein.

Samples

The present invention provides, among other things, methods and compositions for determining the level of one or more glycosaminoglycans or one or more components thereof (e.g., component disaccharides) in a sample. As used herein, the term sample includes a sample as initially collected as well as any later produced variant(s) or portions of that sample, the later produced variants or portions having been derived from that sample, e.g., through any variety of laboratory procedures, the addition of matter, the removal of matter, the modification of components thereof, etc., including through any of the various steps of the present invention. In certain embodiments, a sample is a pooled composite of multiple samples.

In particular embodiments of the present invention, a sample is a biological sample. A biological sample can be any sample including a volume of one or more cells, one or more tissues, one or more bodily fluids, one or more molecules, or one or more substances derived from or having been contacted with a living subject, e.g., a human subject.

In particular instances, a biological sample is cerebrospinal fluid or a component thereof. In particular instances, a biological sample is blood or a component thereof. In particular instances, a biological sample is plasma or a component thereof. In particular instances, a biological sample is urine or a component thereof. In particular instances, a biological sample is fecal matter or a component thereof. In particular instances, a biological sample is saliva, fluids derived from bodily cavities, fluids derived from joints, tears, or any component thereof. In particular instances, a biological sample is a tissue material, such as a sample produced by a tissue biopsy. A tissue material may be derived from any tissue known to those of skill in the art, including, e.g., any of one or more of brain tissue, kidney tissue, liver tissue, lung tissue, hair, nails, reproductive organ tissues, skin, tendon, cartilage or cartilaginous tissues, connective tissue, intestinal mucosa, or muscle tissue. Examples of suitable biological samples include, but are not limited to, serum, urine, stool, saliva, epidermal sample, cheek swab, sperm, cultured cells, bone marrow, buccal cavity scraping, cord blood, chorionic villus sample, chorionic villus sample culture, amniotic fluid, amniotic fluid culture, and/or transcervical lavage fluid.

Cell cultures of any biological samples can also be used as biological samples, e.g., cultures of chorionic villus samples and/or amniotic fluid cultures such as amniocyte cultures. Suitable biological samples may be obtained from a stage of life such as a fetus, young adult, adult (e.g., pregnant women), and the like. Fixed or frozen tissues also may be used.

Biological samples suitable for the inventive may be fresh or frozen samples collected from a subject, or archival samples with known diagnosis, treatment and/or outcome history. Biological samples may be collected by any invasive or non-invasive means, such as, for example, by drawing CSF or blood from a subject, or using fine needle aspiration or needle biopsy, or by surgical biopsy.

In certain instances, a subject of the present invention, e.g., a subject from which is a sample is derived, is an animal. In particular instances, a subject of the present invention, e.g., a subject from which is a sample is derived, is a mammal. In certain instances, a subject of the present invention, e.g., a subject from which is a sample is derived, is a human or a non-human primate. A subject may also be an animal such as a dog, cat, cow, horse, goat, chicken, pig, bird, or fish. The subject may be a veterinary animal, livestock animal, or companion animal. A subject may be a human known to have a GAG condition, diagnosed as having a GAG condition, at risk of having a GAG condition, or in need of diagnosis with respect to a GAG condition. A subject may be an individual in need of treatment for a GAG condition. A subject may be an individual receiving treatment for a GAG condition.

In various embodiments, a sample or biological sample may include or be combined with laboratory reagents. For instance, a sample or biological sample may include a sample as initially derived from a subject in combination with one or more preservatives, excipients, diluents, buffers, or any agent that facilitates analysis of the sample according to a method of the present invention.

Samples or GAGs or components thereof (e.g., component disaccharides) of the present invention can be derived from various sources known to those of skill in the art, including rooster or hen combs or egg shells, e.g., chicken egg shells.

In various embodiments of the present invention, a sample may be treated by any procedure known in the art to increase the concentration of one or more GAGs or one or more components thereof in a sample. Such treatment may occur prior to any or all of, e.g., an extraction step, a cleavage step, a derivatizating step, a separating step, or a detection step or any other series or combination of steps provided herein (e.g., a pretreatment), or may occur at any point between any two steps of a method the present invention, including, e.g., immediately prior to analysis, immediately prior to separation, or immediately prior to detection. Those of skill in the art will appreciate that such treatment can be inclusive of or additional to, or in some instances combined with or coextensive with, any of the various steps, procedures, or methods otherwise described herein.

In various embodiments of the present invention, a sample (e.g., an initially derived sample, a biological sample, an in-process sample, a sample immediately prior to an extraction step, a sample immediately prior to a separation step, or a sample immediately prior to a detection step, e.g., CSF) has a volume of 1 µl to 50 mL or more, e.g., 1 µl, 2 µl, 3 µl, 4 µl, 5 µl, 10 µl, 20 µl, 30 µl, 40 µl, 50 µl, 75 µl, 100 µl, 250 µl, 500 µl, 1 mL, 5 mL, 10 mL, 25 mL, 50 mL, or more, or any range therebetween. For example, in certain embodiments, a sample as provided herein has a volume of 10 µl to 100 µl, e.g., 50 µl.

Samples may be collected at a single time point, at two time points, or at multiple regularly scheduled or irregularly sampled time points over a period of time. For instances, samples may be derived from a subject or group of subjects or selected members of a group of equivalent subjects over a period of time ranging from 10 minutes to 2 years or more, e.g., 10 minutes, 30 minutes, 1 hour, 6 hours, 12 hours, 1 day, 1 week, 1 month, 3 months, 6 months, 1 year, 2 years, or longer, or any range therebetween, e.g., 1 month to 6 months, 6 months to 1 year, or 1 year to 2 years.

Human subjects from which samples are derived as described herein may be, e.g., an embryo, a fetus, a child, or an adult. A child may be, e.g., less than 1 year old, less than 2 years old, less than 3 years old, less than 4 years old, less than 5 years old, less than 6 years old, less than 7 years old, less than 8 years old, less than 9 years old, less than 10 years old, less than 15 years old, or less than 18 years old, or any age therebetween. An adult may be, e.g., more than 18 years old, more than 20 years old, more than 25 years old, more than 30 years old, more than 40 years old, more than 50 years old, more than 60 years old, more than 70 years old, more than 80 years old, or older, or any age therebetween, e.g., 18 to 25 years old, 25 to 30 years old, 30 to 35 years old, 35 to 40 years old, 40 to 50 years old, or 50 to 60 years old. In any embodiments provided herein, unless otherwise indicated, a subject or source of a sample may be a human.

Glycosaminoglycans (GAGs) and GAG Conditions

Glycosaminoglycans (GAGs) constitute a family of generally linear, anionic polymers that are found in organisms, e.g., on cell surfaces, extracellular matrix (ECM) and mast cell granules. GAGs include, e.g., hyaluronan, keratan sulfate (KS), chondroitin sulfate (CS), dermatan sulfate (DS), heparan sulfate (HS), heparin, chondroitin sulfate/dermatan sulfate (CS/DS), and heparan sulfate (HS)/heparin. GAGs fulfill a wide spectrum of biological functions and their metabolism is regulated by multiple factors. Diseases or conditions that result in or are associated with a clinically significant modulation or imbalance of the level of one or more GAGs or one or more components thereof may be referred to as GAG conditions. In various embodiments, a GAG condition is a lysosomal storage disease.

In various embodiments a GAG condition includes dysfunction of one or more enzymes that act directly or indirectly in the regulation of GAG levels, e.g., a gyclosidase, sulfatase, or deacetylase, e.g., a glycan degradation enzyme.

In certain GAG conditions, GAGs can accumulate, e.g., in lysosomes, as a result of disruption, e.g., of enzymes that contribute to GAG degradation, leading to cellular toxicity. GAG conditions include mucopolysaccharidosis (MPS) disorders, which can be recessive inherited disorders that can arise due to a partial or total loss of activity of one or multiple enzymes, e.g., hydrolases, involved in GAG degradation. Without wishing to be bound by any particular scientific theory, at least one known pathway of GAG degradation is thought include nine sequentially acting enzymes. To date, eleven different MPSs have been characterized (MPSI, MPSII, MPSIIIA, MPSIIIB, MPSIIIC, MPSIIID, MPSIVA, MPSIVB, MPSVI, MPSVII and MPSIX).

Sanfilippo syndrome, or mucopolysaccharidosis III (MPSIII), a rare genetic disorder characterized by the deficiency of enzymes involved in the degradation of glycosaminoglycans (GAG). In the absence of enzyme, partially degraded GAG molecules cannot be cleared from the body and accumulate in lysosomes of various tissues, resulting in progressive widespread somatic dysfunction. Four distinct forms of MPSIII, designated MPSIIIA, B, C, and D, have been identified. Each represents a deficiency in one of four enzymes involved in the degradation of the GAG heparan sulfate. All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation.

In a particular example of a GAG condition, Sanfilippo Syndrome A (SanA; MPSIIIA) can result from an aberrant catabolism of HS due to a mutation in the degradation enzyme heparan N-sulfatase (HNS). In SanA, intermediates of HS degradation products can accumulate in the lysosome. While all cell types in the body can be affected, clinical manifestations of SanA include phenotypes related to impaired function of the central nervous system (CNS) and include but are not limited to the deficit in intellectual and language development and motor skills. One treatment strategy for MPS patients is enzyme replacement therapy (ERT) aiming at substituting the deficient hydrolase by a recombinant form of the protein.

In another particular example, Mucopolysaccharidosis type IIIB (MPSIIIB; Sanfilippo B disease) is an autosomal recessive disorder that is characterized by a deficiency of the enzyme alpha-N-acetyl-glucosaminidase (Naglu). In the absence of this enzyme, GAG heparan sulfate accumulates in lysosomes of neurons and glial cells, with lesser accumulation outside the brain.

Deficiency of the enzyme iduronate-2-sulfatase (I2S) in patients with Hunter Syndrome can lead to progressive accumulation of glycosaminoglycans (GAGs), e.g., dermatan sulfate or heparan sulfate, in the lysosomes of a variety of cell types, potentially leading to cellular engorgement, organomegaly, tissue destruction, and organ system dysfunction. Generally, physical manifestations of Hunter Syndrome include both somatic and neuronal symptoms. In some cases of Hunter Syndrome, central nervous system involvement leads to developmental delays and nervous system problems. GAG accumulation in the peripheral tissue can lead to a distinctive coarseness in the facial features of a patient and is responsible for the prominent forehead, flattened bridge and enlarged tongue. Accumulation of GAG can adversely affect the organ systems of the body. Manifesting initially as a thickening of the wall of the heart, lungs and airways, and abnormal enlargement of the liver, spleen and kidneys, these profound changes can ultimately lead to widespread catastrophic organ failure. Hunter Syndrome is typically severe, progressive, and life-limiting.

In various embodiments a GAG condition is a lysosomal storage disorder, e.g., a lysosomal storage disorder selected from MPSI, MPSII, MPSIIIA, MPSIIIB, MPSIIIC, MPSIIID, MPSIVA, MPSIVB, MPSVI, MPSVII, MPSIX, alpha mannosidosis, aspartylglucosaminuria, Fabry, fucosidosis, galactosialidosis, Gaucher disease, GM1 gangliosidosis, GM2 activator deficiency, sialidosis, Krabbe, metchromatic leukodystrophy, mucolipidosis IV, multiple sulfatase deficiency, Pompe, Sandhoff, Tay-Sachs, AB Variant Schindler Disease, Salla Disease, beta mannosidosis, or globoid cell leukodystrophy. Those of skill in the art will appreciate that these conditions may only be relevant to the present invention to the extent that they encompass a change, modification or disruption in the level of one or more GAGs, components thereof or cleavage products thereof. In various embodiments, the present invention can include or constitute, without limitation, a mechanism for assessing the activity of an enzyme relevant to a GAG condition, assessing the status of a GAG condition, or the monitoring of treatment efficacy in connection with a GAG condition, e.g., in a subject in need thereof or for research purposes.

Extraction

In various embodiments of the present invention, a sample is processed by extraction (e.g., purification or isolation) of one or more GAGs (e.g., HS) or one or more components thereof (e.g., component disaccharides). GAGs include, e.g., hyaluronan, keratan sulfate (KS), chondroitin sulfate (CS), dermatan sulfate (DS), heparan sulfate (HS), heparin, chondroitin sulfate/dermatan sulfate (CS/DS), and heparan sulfate (HS)/heparin. In particular embodiments the extraction is a process that isolates or purifies one or more GAG molecules, or one or more components thereof, from one or more other molecules or types of molecules present in the sample.

Various methods of for the extraction of one or more GAGs or one or more components thereof from a sample are known in the art. Also known in the art are methods for extraction of one or more particular GAGs or one or more particular components thereof.

In various embodiments, an extraction step of the present invention can include fractionation, gradient or spin column centrifugation, centrifugation, electrophoresis, chromatography (e.g., silica gel chromatography, alumina column chromatography, chiral column HPLC, achiral column HPLC, thin layer chromatography, preparative flash chromatography, gel filtration chromatography, permeation chromatography, size exclusion chromatography, molecular sieve chromatography, affinity chromatography, or any other method of chromatography provided herein in this or any other context, filtration (e.g., through a florisil plug or activated charcoal plug), precipitation, osmosis, recrystallization, fluorous phase purification, distillation, chromatofocusing, supercritical fluid extraction, or any other applicable technique known in the art.

Extraction can include digestion with a proteinase, e.g., papain. Extraction can include a precipitation step including, e.g., ethanol (e.g., ethanol at varying concentrations). Extraction can include alcohol fractionation. Extraction can include chromatography, e.g., anion exchange chromatography, DEAE-Sephacel ion-exchange chromatography, SEPHAROSE® chromatography, or gel filtration chromatography, or any technique of chromatography provided herein or otherwise known to those of skill in the art. Extraction can include solubilization of one or more GAGs or one or more components thereof having been precipitated as GAG/GAG molecule-quaternary ammonium compound complexes with different concentrations of NaCl. Extraction can include selective precipitation, e.g., with copper sulfate under alkaline conditions. Extraction can include a step of diafiltration or dialysis. Extraction of one or more GAGs or one or more components thereof can include treatment with acetate. Further methods of GAG or GAG molecule extraction are known in the art.

Particular GAGs or components thereof (e.g., component disaccharides) can be isolated based upon affinity to a known binding moiety or binding partner, such as bone morphogenetic protein 2.

Extraction of one or more GAGs or one or more components thereof from a sample may require breakdown of other tissue components or associated tissue components to which the one or more GAGs or one or more components thereof may be, e.g., covalently linked. Extraction of one or more GAGs or one or more components thereof can include a hydrolysis treatment. Extraction of one or more GAGs or one or more components thereof can include incubation with detergent. Extraction of one or more GAGs or one or more components thereof can include alkali treatment.

In certain embodiments, a method of GAG or GAG component extraction is a DEAE extraction. In particular instances, a method of GAG extraction is a DEAE extraction in which samples are contacted with DEAE, optionally washed with a loading buffer such that one or more GAGs or one or more components thereof are not eluted, and then contacting the sample with an elution buffer such that the one or more GAGs or one or more components thereof are eluted.

In various embodiments, extraction, isolation, or purification includes or results in the partial, nearly-complete, or complete removal of one or more of monosaccharides, sulfates, phosphates, acetate, sialic acid, or any component that may be recognized as a contaminant by those of skill in the art, such as, in some instances, a component that is not a GAG, a component thereof (e.g., a component disaccharide), or a cleavage product thereof.

In certain embodiments, GAGs are extracted by ion exchange solid-phase extraction of heparan sulfate.

In particular instances, the extraction produces an extracted sample having an increase in the absolute or relative concentration of one or more GAG molecules or one or more components thereof (as measured, e.g., by molarity or weight) by 5% or more, e.g., 5%, 10%, 20%, 30%, 40%, 50%, 60%, 70%, 80%, 90%, 2-fold (i.e., an increase of 100%), 3-fold, 4-fold, 5-fold, 10-fold, 50-fold, 100-fold, 1,000-fold, 1,000,000 fold, or more, or any range therebetween. For instance, extraction may increase the absolute or relative concentration of one or more GAG molecules or one or more components thereof (as measured, e.g., by molarity or weight) by 20% to 100%, 20% to 2-fold, 20% to five-fold, 50% to 100%, 50% to 2-fold, 50% to 5-fold, 1-fold to 5-fold, 1-fold to 100-fold, 50-fold to 100-fold, 100-fold to 1,000-fold, or 1,000-fold to 1,000,000 fold.

In particular instances, an extracted sample has a total amount of one or more GAG molecules or one or more components thereof that is above the lower limit of detection according to at least one method of the present invention. For instance, in certain embodiments, the extracted sample can include of 0.01 to 100 or more µM of a particular GAG or component thereof (e.g., a component disaccharide), or of total disaccharide, e.g., 0.01, 0.05, 0.1, 0.15, 0.2, 0.3, 0.4, 0.5, 1, 2, 3, 4, 5, 10, 20, 30, 40, 50, 100, 200, 300, 400, 500 or more µM of a particular molecule or of total disaccharide.

Desalting

In various embodiments of the present invention, a sample is processed by desalting. In various embodiments, desalting can occur after extraction. In various embodiments, desalting can occur before extraction. In various embodiments, desalting occurs in-line with extraction. In various embodiments, extraction and desalting are simultaneous, e.g., occurring together as the result of a single step.

In certain embodiments, desalting includes gel filtration and/or gel filtration chromatography. In certain embodiments, desalting includes the use of a gravity-flow column, chromatography cartridges, gel filtration columns or media, or centrifuge or spin columns. In certain embodiments, desalting includes diafiltration, e.g., diafiltration using ultrafiltration membranes, selectively permeable membranes, or other filtration media. In particular embodiments, the diafiltration includes continuous diafiltration or constant volume diafiltration, or discontinuous diafiltration. Desalting can include concentrators, dialysis cassettes or units, desalting columns, or buffer-exchange devices. In certain embodiments, desalting includes DEAE chromatography or chromatography with a DEAE conjugate. In some embodiments, desalting can include an evaporation step followed by treatment with alcohol and/or ammonium acetate.

In particular examples, a sample (e.g., a biological sample or an extracted sample) is added to a desalting plate such as a G-25 Multitrap plate and the plate is centrifuged such that the eluent is a desalted sample.

In some instance, desalting includes one or more of various buffers known in the art for use in or in conjunction with desalting and related processes. Kits and components for use in desalting and related processes are also commercially available. For instance, commercially available gel filtration products include SEPHADEX® G-10, SEPHADEX® G-25, Bio-Gel P-60, SEPHADEX® G-75, SEPHADEX® G-100, Bio-Gel P-100, SEPHADEX® G-200, Bio-Gel P-200, SEPHACRYL® S-300, and SEPHAROSE® 2B. Known buffers include, e.g., Tris-HCl, sodium phosphate, and sodium acetate. Various buffers may be prepared to any appropriate or conditionally optimized pH or other characteristic.

In various embodiments, desalting includes dialysis or buffer exchange.

The desalted product can be evaporated, for example under vacuum and/or at 50° C.

In certain instances, the desalting step is an in-line desalting step. An in-line desalting step can eliminate the need to separately desalt a sample prior to separation and/or detection. In certain embodiments, the present invention includes direct injection of a sample to an apparatus including in-line desalting, e.g., an apparatus including a precolumn and separation or analytical column, e.g., an apparatus including a precolumn directly joined to a separation or analytical column. In particular instances, an apparatus including in-line desalting can include a reverse phase precolumn and an anion exchange column. The reverse phase precolumn, in some instances, may be utilized to trap lipids. In certain embodiments, the apparatus for in-line desalting includes a reverse phase pre-column joined to an anion exchange column, e.g., directly joined to an anion exchange column. In various embodiments including in-line desalting, the desalting occurs in-line with extraction, in-line with separation, or in-line with analysis.

Enzymatic Digestion

Various embodiments of the present invention include a step in which one or more GAGs are enzymatically cleaved to yield GAG components such as disaccharides. GAGs include, e.g., hyaluronan, keratan sulfate (KS), chondroitin sulfate (CS), dermatan sulfate (DS), heparan sulfate (HS), heparin, chondroitin sulfate/dermatan sulfate (CS/DS), and heparan sulfate (HS)/heparin. The group of enzymes known as GAG lyases includes examples of enzymes that digest GAG molecules. Broadly, the present invention includes, as a class, among other enzymes, enzymes known to specifically cleave GAGs. Specificity in the cleavage of GAG molecules can optionally be achieved through the selection of particular digestion enzymes. Examples include chondroitin sulfate lyases, chondroitinase ABC, chondroitinase C, chondroitinase C from *Flavobacterium heparinum*, heparan sulfate lyases, streptococcal hyaluronidase, *Streptomyces* hyaluronidase, hyaluronidase A, hyaluronidase C, testicular hyaluronidase, keratanase, testicular hyaluronidase from sheep testes, and endo-β-galactosidase. Various enzymes of broader or narrower, or conditionally broader or narrower, specificity are known in the art. The specificities of such enzymes are known to those of skill in the art. In various embodiments, digestion produces GAG cleavage products.

As will be appreciated by those of skill in the art heparinase I, heparinase II, and heparinase III are enzymes able to cleave heparan sulfate. Chondroitinase AC, chondroitinase B, and chondroitinase C, as well as chondroitinase ABC, are able to cleave chondroitin sulfate and/or dermatan sulfate. Keratanase II is able to cleave keratan sulfate. Hyaluronidase is able to cleave hyaluronic acid.

For instance, heparinase I is an enzyme that digests certain GAGs including heparan and related molecules. Without wishing to be bound by any particular scientific theory, it is thought that heparinase I, under at least certain conditions, is able to participate in eliminative cleavage of polysaccharides containing 1,4-linked D-glucuronate or L-iduronate residues and 1,4-a-linked 2-sulfoamino-2-deoxy-6-sulfo-D-glucose residues to give oligosaccharides with terminal 4-deoxy-a-D-gluc-4-enuronosyl groups at their non-reducing ends, and that heparinase I cleaves heparin more readily than it cleaves heparan sulfate.

Again, without wishing to be bound by any particular scientific theory, it is thought that heparinase II cleaves both heparin and heparan sulfate.

Again, without wishing to be bound by any particular scientific theory, heparinase III is thought to cleave heparan sulfate exclusively and is thought not to cleave unfractionated heparan or low molecular weight heparans.

Again, without wishing to be bound by any particular scientific theory, chondroitinase ABC, or chondroitin ABC lyase, e.g., from *Proteus vulgaris*, is thought to be capable of digesting all types of chondroitin sulfate, dermatan sulfate, and hyaluronan. Without wishing to be bound by any particular scientific theory, it is thought that chondroitinase ABC catalyzes the eliminative cleavage of N-acetylhexosaminide linkages in, e.g., chondroitin 4-sulfate, chondroitin 6-sulfate, dermatan sulfate, chondroitin, and hyaluronic acid, yielding various disaccharides. It is thought that this enzyme does not act on keratin sulfate, heparin, and heparan sulfate.

Again, without wishing to be bound by any particular scientific theory, Chondroitinase AC II Arthro, or chondroitin AC lyase, e.g., from *Arthrobacter aurescens*, is thought to digest all types of chondroitin sulfate and hyaluronan, but not dermatan sulfate. Without wishing to be bound by any particular scientific theory, it is thought that chondroitinase AC catalyzes the eliminative cleavage of N-acetylhexosaminide linkages in chondroitin, chondroitin 4-sulfate, and chondroitin 6-sulfate, yielding various disaccharides.

Again, without wishing to be bound by any particular scientific theory, hyaluronidase, or hyaluronate lyase, from Streptomycles hyalurolycticus is thought to specifically digest hyaluronan or hyaluronic acid. Hyaluronidase SD, or hyaluronate lyase, from *Streptococcus dysgalactiase* is thought to digest unsulfated chondroitin and hyaluronan. In still other instances, hyaluronidase enzymes digest all types of chondroitin sulfate and hyaluronan.

In other embodiments, a digestion of the present reaction includes one or more enzymes that do not cleave heparan or heparan sulfate. For instance, without wishing to be bound by any particular scientific theory, the enzyme chondroitinase AC is thought to participate in the eliminative degradation of polysaccharides containing 1,4-b-D-hexosaminyl and 1,3-b-D-glucuronosyl linkages to disaccharides containing 4-deoxy-b-D-gluc-4-enuronosyl groups, and is thought to cleave chondroitin sulfates A and C. Chondroitinase B is thought to cleave dermatan sulfate.

In various embodiments of the present invention, a sample, or one or more GAGs or components thereof, is contacted with one or more GAG-digesting enzymes, e.g., any of one or more of the GAG-digesting enzymes provided herein or otherwise known in the art.

A digestion reaction of the present invention may include GAG at concentration, e.g., of 0.01 to 100 or more μM of a particular molecule or of total disaccharide, e.g., 0.01, 0.05, 0.1, 0.15, 0.2, 0.3, 0.4, 0.5, 1, 2, 3, 4, 5, 10, 20, 30, 40, 50, 100, 200, 300, 400, 500 or more μM of a particular molecule or of total disaccharide.

A digestion reaction of the present invention may include a GAG-digesting enzyme at 0.1 U to 100 U or more, e.g., 0.1 U, 0.5 U, 1 U, 2 U, 3 U, 4 U, 5 U, 10 U, 20 U, 30 U, 40 U, 50 U, 75 U, 100 U or more, or any range therebetween, e.g., 0.1 U to 20 U, 0.5 U to 10 U, or 1 U to 5 U.

A digestion reaction can proceed for 30 seconds to 6 days or more, e.g., 30 second, 1 minute, 5 minutes, 30 minutes, 1 hour, 2 hours, 3 hours, 4 hours, 5 hours, 6 hours, 12 hours, 1 day, 2 days, 3 days, 4 days, or more, or any range therebetween. The reaction can occur, e.g., at a temperature between 1° C. and 99° C., such as 1° C., 5° C., 10° C., 20° C., 30° C., 40° C., 50° C., 60° C., 70° C., or any range therebetween.

A digestion reaction of the present invention may be incubated for a period of time sufficient to allow one or more GAGs (e.g., HS) or one or more components thereof (e.g., component disaccharides) to be cleaved by a GAG-digesting enzyme. For instance, a digestion reaction of the present invention may be incubated for 10 seconds or more, e.g., 10 seconds, 20 seconds, 30 seconds, 40 seconds, 50 seconds, 1 minute, 2 minutes, 3 minutes, 4 minutes, 5 minutes, 10 minutes, 20 minutes, 40 minutes, 60 minutes, 2 hours, 3 hours, 4 hours, 5 hours, 6 hours, 12 hours, 1 day, 2 days, or longer, or any range therebetween, under various conditions. Digestion may be complete or incomplete, e.g., digestion may include cleavage of 1% to 100% of GAG or GAG components capable of being degraded by a particular enzyme, e.g., 1%, 2%, 3%, 4%, 5%, 10%, 15%, 20%, 30%, 40%, 50%, 60%, 70%, 80%, 90%, 95%, 96%, 97%, 98%, 99%, or 100% or any range therebetween, e.g., 30% to 100%, 40% to 100%, 50% to 100%, 60% to 100%, 70% to 100%, 80% to 100%, or 90% to 100%.

Derivatization

In various embodiments, samples of the present invention can be derivatized. In particular instances, GAG cleavage products present in a digested sample are derivatized. Derivatization can increase the sensitivity of an analysis of various methods provided herein, e.g., by contributing to the chromatographic separation of derivatized molecules, e.g., the separation of derivatized GAG cleavage products.

In various embodiments derivatization includes the addition of a derivatization moiety at multiple sites along a GAG molecule or cleavage product thereof. In various embodiments, derivatization includes the addition of a derivatization moiety at a particular site on a GAG molecule or cleavage product thereof.

A sample may be derivatized prior to an extraction step or after an extraction step. A sample may be derivatized prior to a digestion step or after a digestion step. A sample may be derivatized at a time that is prior to an extraction step and prior to a digestion step. A sample may be derivatized at a time that is after an extraction step and after a digestion step. A sample may be derivatized at a time that is between an extraction step and a digestion step, e.g., subsequent to extraction but prior to digestion, or, e.g., subsequent to digestion but prior to extraction. In various embodiments, a method of the present invention can include, e.g., an extraction step followed by a digestion step followed by a derivatization step.

Derivatization can include the addition of a hydrophobic moiety to GAG cleavage products. Derivatization can include the addition of a moiety such as 2-aminopyridine, 2-aminobenzamide (AB), 2-aminobenzoic acid (AA), 4-amino-salicylic acid (ASYL), 3-aminoquinolone (3-AQ), 3-(acetylamino)-6-aminoacridine (AA-Ac), 2-aminoacridone (AMAC), procaine (Pro), procainamide (ProA), ethyl-4-amino-benzoate (ABEE), Butyl-4-amino-benzoate (ABBE), 5-Amino-2-naphthalene-sulfonic acid (ANSA), 8-aminonaphthalene-1,3,6-trisulfonic acid (ANTS), 8-aminopyrene-1,3,6-trisulfonic acid (APTS), 1-phenyl-3-methyl-5-pyrazolone (PMP), 4-nitro-2,1,3-benzoxadiazole (NBD-F), Fmoc, and 6-aminoquinoline (see, e.g. Pabst et al. 2009 *Analytical Biochemistry* 384: 263-273).

Those of skill in the art will be aware of various moieties for derivatizing molecules (e.g., molecules such as GAG cleavage products) for separation, e.g., chromatographic separation, such that addition of the moiety contributes to the separation and thereby improves the sensitivity of detection. Those of skill in the art will further appreciate that particular derivatization moieties, e.g., hydrophobic derivatization moieties, may be selected in accordance with the method of separation, e.g., chromatography, e.g., anion exchange chromatography.

A derivatization reaction can proceed for 30 seconds to 6 days or more, e.g., 30 second, 1 minute, 5 minutes, 30 minutes, 1 hour, 2 hours, 3 hours, 4 hours, 5 hours, 6 hours, 12 hours, 1 day, 2 days, 3 days, 4 days, or more, or any range therebetween. The derivatization reaction can occur at a temperature between 1° C. and 99° C., such as 1° C., 5° C., 10° C., 20° C., 30° C., 40° C., 50° C., 60° C., 70° C., 80° C., 90° C., or 99° C., or any range therebetween.

Glycan-Specific Extraction

In various embodiments, a glycan-specific extraction step may be applied at any point in a method of the present invention, e.g., after a digestion or derivatization but prior to analyzing. In particular embodiments, a glycan-specific extraction step may be a glycan-specific solid-phase extraction step. When present, a glycan-specific extraction step may a second extraction step. Alternatively, when present, a late extraction step may be the only extraction step. A glycan-specific extraction step may employ any of the methods or techniques described herein or otherwise known to the art, particularly those methods or techniques identified with respect to any other extraction step, conditional, optional, or otherwise.

Analyzing

Samples of the present invention, e.g., samples that have been extracted, desalted, and/or digested, e.g., samples that have been at least extracted and digested, may be analyzed in order to identify from the sample the type and/or amount of one or more GAGs (e.g., HS) or one or more components or cleavage products thereof present in the sample. In particular instances, a digested sample is analyzed to determine the type and amount of one or more GAGs having been initially present in the sample prior to digestion by identifying cleavage products present in the sample after digestion. Analyzing may include a step of separating one or more GAGs or one or more components or cleavage products thereof present in a digested and/or derivatized sample. In particular instances, the present invention includes separating derivatized GAG cleavage products.

Analyzing may include a step of detecting one or more GAGs (e.g., HS) or one or more components or cleavage products present in a digested and/or derivatized sample. In particular embodiments, analyzing may include detecting one or more derivatized GAG cleavage products.

In particular embodiments, analyzing may include a step of separating one or more GAGs or one or more components or cleavage products thereof present in a digested and/or derivatized sample followed by a step of detecting one or more separated GAGs or one or more separated GAG components or on or more separated cleavage products. In still more particular embodiments, analyzing may include separating one or more derivatized GAG cleavage products and detecting one or more of the separated GAG cleavage products.

Separation

Samples of the present invention, e.g., samples that have been extracted, desalted, digested, and derivatized, e.g., in that order, may be treated in a manner that separates one or more GAGs or one or more components or cleavage products thereof.

Various methods of separation are known in the art and include, as examples, gel-based methods of separation and chromatographic methods of separation. In particular instances, the method of separation may include liquid chromatography, thin-layer chromatography, capillary electrophoresis, gas chromatography, or solvent extraction. In some instances, the method of separation may include adsorption chromatography, partition chromatography, normal-phase chromatography, aqueous normal phase chromatography, reverse-phase chromatography, ion exchange chromatography, molecular or size exclusion chromatography, or affinity chromatography. The method of separation may include ultra-performance liquid chromatography (UPLC) or high-performance liquid chromatography (HPLC). The method of separation may include high performance anion exchange chromatography (HPAEC). Methods of HPLC, HPAEC, and UPLC are known in the art. A method of separation including chromatography may include a hydrophilic interaction liquid chromatography (HILIC), reversed phase (RP) chromatography, or charged surface hybrid (CSH) column chromatography. In various embodiments the chromatography includes beads, e.g., anion exchange beads. In some instances, separation will include one or more steps in which molecules are distinguished based on, e.g., size, polarity, hydrophobicity, charge, fluorescence, radioactivity, spectrophotometric characteristics, spectra, mass, or other characteristics known in the art, or any combination thereof. Any combination of any two or more methods of separation is contemplated herein (e.g., multidimensional separation).

Detection

Separated or unseparated samples may be subjected to a detection step. In certain embodiments, detection includes mass spectrometry in one or more of its various forms. In some embodiments, a detection step may include, e.g., conductivity detection, gas chromatographic detection, amperometric detection (e.g., pulsed amperometric detection (PAD) or 3D amperometry), gel electrophoresis and other traditional protein analysis methods, mass spectrometry in any of its various forms, as well as other methods known in the art.

Methods of mass spectrometry applicable to the present invention can include any method of mass spectrometry known in the art. For instance, detection of one or more GAGs or one or more components or cleavage products thereof can utilize accelerator mass spectrometry (AMS), gas chromatography-mass spectrometry (GC-MS), liquid chromatography-mass spectrometry (LC-MS), inductively coupled plasma-mass spectrometry (ICP-MS), isotope ratio mass spectrometry (IRMS), ion mobility spectrometry-mass spectrometry, matrix assisted laser desorption ionization (MALDI) mass spectrometry (.e.g., MALDI-TOF), surface enhanced laser desorption ionization (SELDI) mass spectrometry (e.g., SELDI-TOF), tandem mass spectrometry (MS/MS), thermal ionization-mass spectrometry (TIMS), spark source mass spectrometry (SSMS), fast atom bombardment mass spectrometry (FAB), soft laser desorption (SLD) mass spectrometry, atmospheric pressure chemical ionization (APCI) mass spectrometry, secondary ion mass spectrometry (SIMS), spark ionization (IS) mass spectrometry, thermal ionization (TI) mass spectrometry, chemical ionization (CI) mass spectrometry, electron impact (EI) mass spectrometry, field desorption/field ionization (FD/FI) mass spectrometry, and thermospray ionization (TSP) mass spectrometry. Those of skill in the art will be acquainted with the various forms of mass spectrometry.

Mass spectrometry can include an ionization source, an analyzer, and a detector. The mass spectrometry analyzer can be selected from any analyzer known in the art, e.g., quadrupole mass analyzers, time of flight mass analyzers, magnetic sector mass analyzers, electrostatic sector mass analyzers, quadrupole ion trap mass analyzers, orbitrap analyzers, or ion cyclotron resonance analyzers. The mass spectrometry detector can be selected from any detector known in the art, e.g., a photomultiplier, electron multiplier, Faraday cups, or microchannel plate or array detector.

In various methods described herein, a method of the present invention includes LC/MS or LC/MS/MS.

In certain instances, a detection step of the present invention can include, instead of or in combination with mass spectrometry, gas chromatography. Gas chromatography detectors can include non-selective, selective, specific, concentration dependent, or mass flow dependent detectors. Particular types of detectors can include flame ionization detectors, thermal conductivity detectors, electron capture detectors, and nitrogen phosphorous detectors. In particular instances, the present invention includes gas chromatograph mass spectrometry (GCMS).

In various embodiments, the detection step can include, instead of or in combination with mass spectrometry or any other detection mechanism provided herein, nuclear magnetic resonance, spectrometry, radiation spectrometry, thin layer chromatography or related techniques, or other methods known in the art, including without limitation the use of moieties capable of functioning as probes specific to a particular GAG, component thereof, cleavage product thereof, or any plurality selected from any GAG, component thereof (e.g., a component disaccharide), or cleavage product thereof as would be understood by those of skill in the art to be included within the scope of the present invention.

Any combination of any two or more methods of detection is contemplated herein (e.g., multidimensional detection).

In various embodiments, samples are combined with a solution of tributylamine in acetonitrile prior to detection.

In various embodiments, the analysis of samples of the present invention, e.g., samples that have been digested and derivatized, includes both a separation step and a detection step.

In various embodiments of the present invention, a method of determining the level of one or more GAGs (e.g., HS) includes the steps of extracting, desalting, digesting, derivatizing, separating, and detecting as described herein, optionally in that order. In various embodiments of the present invention, a method of determining the level of one or more GAGs includes the steps of extracting, digesting, derivatizing, separating, and detecting as described herein. In various embodiments of the present invention, a method of determining the level of one or more GAGs includes the steps of desalting, digesting, derivatizing, separating, and detecting as described herein, optionally in that order. In various embodiments of the present invention, a method of determining the level of one or more GAGs includes the steps of digesting, derivatizing, separating, and detecting as described herein, optionally in that order. In various embodiments of the present invention, a method of determining the level of one or more GAGs includes the steps of desalting, extracting, digesting, derivatizing, separating, and detecting as described herein, optionally in that order. Various embodiments of the present invention include any combination of steps provided herein, and in any order, including the optional exclusion of any steps provided herein or optional inclusion of multiple steps of a particular type or function.

Those of skill in the art will appreciate that various embodiments of the present invention include detection (e.g., by mass spectrometry) of multiple GAG cleavage products, e.g., multiple distinct cleavage products derived from a particular GAG or component thereof. Further, various embodiments of the present invention can encompass the detection of multiple distinct GAGs from a single sample or in a single group of reactions or from a single reaction. The present invention encompasses the recognition that in various instances measuring any single GAG cleavage product may be sufficiently diagnostic to provide the function or utility of the invention as disclosed herein, or in various embodiments a valuable portion thereof. Moreover, any subset of the total possible range of detectable GAG cleavage products from a single sample may be detected and therein provide the function or utility of the invention as disclosed herein, or in various embodiments a valuable portion thereof. The present invention does not require that all GAGs, GAG components, or GAG cleavage products present in a sample be detected or measured. The present invention also encompasses embodiments in which all GAGs, GAG components, or GAG cleavage products present in a sample be detected or measured.

An advantage of the various embodiments of the present invention is an increase in the precision of detection, and thereby an increase in the precision of measuring the level of one or more GAGs, the level of one or more components thereof, or the level of one or more GAG cleavage products.

Controls and Standards

In various embodiments, methods of analysis as described herein will include controls and/or internal standards. The selection of controls and/or internal standards is generally known to those of skill in the art. Comparison of analysis results to controls and/or internal standards can provide a basis for drawing conclusions and/or identifying critical data points. As used herein, the term control or standard (or controls or standards) will be understood to mean any single reaction or datum, plurality of reactions or data, constellation of reactions or data, or any expression or integration thereof.

In various embodiments of the present invention, analysis includes an internal standard where the internal standard includes one or more molecules known to be produced by the cleavage of one or more GAG molecules in the presence of one or more GAG cleavage enzymes.

For instance, an internal standard can be a GAG cleavage product or a molecule having the formula of a GAG cleavage product, e.g., a saccharide or disaccharide. An internal standard GAG cleavage product can be, e.g., a molecule having the formula of a heparan sulfate cleavage product, e.g., a heparan sulfate cleavage product selected from I-S (ΔUA,2S-GlcNS,6S; calculated MW 665.3975), II-S (ΔUA-GlcNS,6S; calculated MW 563.3533), III-S (ΔUA,2S-GlcNS; calculated MW 563.3533), IV-S (ΔUA-GlcNS; calculated MW 461.3091), II-A (ΔUA-GlcNAc,6s; calculated MW 503.3463), and IV-A (ΔUA-GlcNAc; calculated MW 401.3022), the structures of which are provided below. Controls or standards may be synthesized, purchased, or produced by the cleavage of GAG molecules.

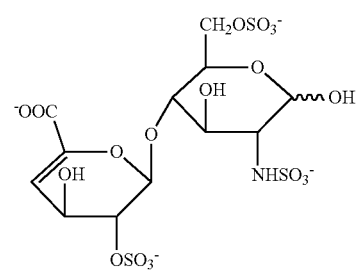

I-S

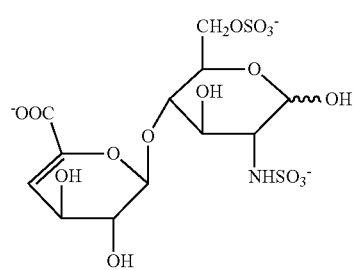

II-S

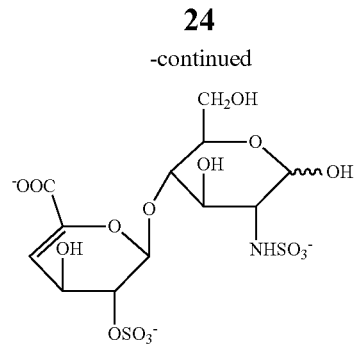

III-S

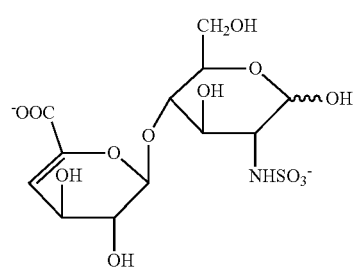

IV-S

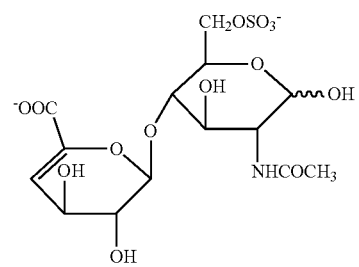

II-A

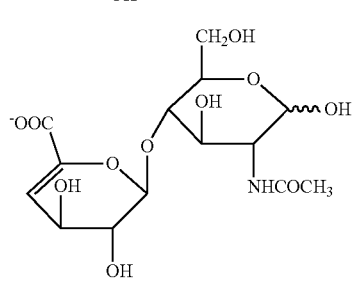

IV-A

In various embodiments, an internal standard is modified to enable or includes a modification that enables detection. For instance, in certain embodiments, sample is derivatized with a particular molecule while internal standards are derivatized with an isotopically labeled version, e.g., a heavy version, of that particular molecule. For example, in some instances sample is derivatized with 4-Butylaniline and one or more internal standard molecules are derivatized with $^{13}C_6$-4-Butylaniline.

Any of one or more controls internal standards may be provided at a gradient of concentrations. For instance any of one or more controls or internal standards may be provided at a concentration of 0.01 to 100 or more μM of a particular molecule or of total disaccharide, e.g., 0.01, 0.05, 0.1, 0.15, 0.2, 0.3, 0.4, 0.5, 1, 2, 3, 4, 5, 10, 20, 30, 40, 50, 100, 200, 300, 400, 500 or more μM of a particular molecule or of total disaccharide.

In various embodiments, a standard consists of a single disaccharide, e.g., a single disaccharide produced by the cleavage of one or more particular GAGs by one or more particular enzymes included in a method as described herein. In various embodiments, a standard consists of two or more disaccharides, e.g., two or more disaccharides produced by the cleavage of one or more particular GAGs by one or more particular enzymes included in a method as described herein. In various embodiments, such two or more disaccharides may be analyzed in a single reaction mixture or in multiple reaction mixtures. In various embodiments, two or more disaccharides are included in the standard at varying levels.

In particular embodiments, the individual levels of one or more (e.g., two or more, e.g., six) disaccharide standards may be selected such that the individual levels of the two or more disaccharide standards match, approximate, or reflect a normal or substantially normal level, an experimentally determined normal level, a canonical normal level, a sample-specific normal level, a sample group-specific normal level, a population specific normal level, or a condition-specific normal level. In particular embodiments, the individual levels of one or more (e.g., two or more, e.g., six) disaccharide standards may be selected such that the individual levels of the two or more disaccharide standards match, approximate, or reflect a value that falls within a normal or substantially normal range, an experimentally determined normal range, a canonical normal range, a sample-specific normal range, a sample group-specific normal range, a population specific normal range, or a condition-specific normal range. In particular embodiments, the individual levels of one or more (e.g., two or more, e.g., six) disaccharide standards may be selected such that the individual levels of the two or more disaccharide standards fall within a normal or substantially normal range, an experimentally determined normal range, a canonical normal range, a sample-specific normal range, a sample group-specific normal range, a population specific normal range, or a condition-specific normal range. In various embodiments, the level of one or more disaccharide standards is within 1%, 2%, 3%, 4%, 5%, 10%, 15%, 20%, 25%, 30%, 40%, 50%, 60%, 70%, 80%, 85%, 90%, 91%, 92%, 93%, 94%, 95%, 96%, 97%, 98%, 99%, or 100% of any such level or any such range.

In particular embodiments, a method of the present invention includes six standards. In still more particular embodiments, the six standards are IS, IIS, IIIS, IVS, IIA, and IVA. The present invention further includes any subset thereof, applied, for example, as described herein, including respective independently determined molar percent ratios. These six standards may be present in a single mixture, in individual mixtures, or in any combination thereof, including a plurality of different combined or individual mixtures.

In any such embodiments, including embodiments in which IS, IIS, IIIS, IVS, IIA, and IVA are present in a single mixture, the molar percent ratio of IS can be 0.5% to 100%, e.g., 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, 90%, or 100% or any range therebetween (e.g., 1% to 20%, 5% to 15%, or 8% to 12%). In various such embodiments, the molar percent ration of IS can be 10%.

In any such embodiments, including embodiments in which IS, IIS, IIIS, IVS, IIA, and IVA are present in a single mixture, the molar percent ratio of IIS can be 0.5% to 100%, e.g., 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, 90%, or 100% or any range therebetween (e.g., 1% to 20%, 1% to 15%, 1% to 10%, 3% to 8%, or 3% to 6%). In various such embodiments, the molar percent ratio of IIS can be 5%.

In any such embodiments, including embodiments in which IS, IIS, IIIS, IVS, IIA, and IVA are present in a single mixture, the molar percent ratio of IIIS can be 0.5% to 100%, e.g., 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, 90%, or 100% or any range therebetween (e.g., 1% to 30%, 5% to 25%, 10% to 20%, 12% to 18%, or 13% to 17%). In various such embodiments, the molar percent ratio of IIIS can be 15%.

In any such embodiments, including embodiments in which IS, IIS, IIIS, IVS, IIA, and IVA are present in a single mixture, the molar percent ratio of IVS can be 0.5% to 100%, e.g., 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, 90%, or 100% or any range therebetween (e.g., 1% to 20%, 5% to 15%, or 8% to 12%). In various such embodiments, the molar percent ratio of IVS can be 10%.

In any such embodiments, including embodiments in which IS, IIS, IIIS, IVS, IIA, and IVA are present in a single mixture, the molar percent ratio of IIA can be 0.5% to 100%, e.g., 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, 90%, or 100% or any range therebetween (e.g., 1% to 20%, 5% to 15%, or 8% to 12%). In various such embodiments, the molar percent ratio of IIA can be 10%.

In any such embodiments, including embodiments in which IS, IIS, IIIS, IVS, IIA, and IVA are present in a single mixture, the molar percent ratio of IVA can be 0.5% to 100%, e.g., 1%, 5%, 10%, 15%, 20%, 25%, 30%, 35%, 40%, 45%, 50%, 55%, 60%, 65%, 70%, 75%, 80%, 90%, or 100% or any range therebetween (e.g., 20% to 80%, 30% to 70%, 35% to 65%, 40% to 60%, or 45% to 55%). In various such embodiments, the molar percent ratio of IVA can be 50%.

Accordingly, in particular embodiments of the present invention, IS, IIS, IIIS, IVS, IIA, and IVA, can be mixed together in the following respective molar percent ratios: 10%, 5%, 15%, 10%, 10% and 50%. Those of skill in the art will understand that, in various instances as presented herein, and particular instances wherein a plurality of distinct disaccharides are present in a single mixture, that the net percent molar ratio of those disaccharides (or groups of disaccharides when so identified with respect to the percentage(s)) will be 100%. As will be understood by those of skill in the art, in various instances of the present invention, a mixture of disaccharide standards will include other compounds or molecules not relevant to the function of serving as a standard and these other compounds or molecules not relevant to the function of serving as a standard will be excluded from the calculation of percent molar ratio.

In various embodiments, the accuracy of the present methods with respect to the measurement of the level of one or more GAGs, components thereof, cleavage products thereof, or GAG molecules is greater than +/−20%, e.g., greater than +/−20%, +/−19%, +/−18%, +/−17%, +/−16%, +/−15%, +/−14%, +/−13%, +/−12%, +/−11%, +/−10%, +/−9%, +/−8%, +/−7%, +/−6%, +/−5%, +/−4%, +/−3%, +/−2%, +/−1%, or greater than +/−1%, or any range therebetween. In various embodiments, the precision of the present methods with respect to the measurement of the level of one or more GAGs, components thereof, cleavage products thereof, or GAG molecules is from 0% to 20%, from 0% to 19%, from 0% to 18%, from 0% to 17%, from 0% to 16%, from 0% to 15%, from 0% to 14%, from 0% to 13%, from 0% to 12%, from 0% to 11%, from 0% to 10%, from 0% to 9%, from 0% to 8%, from 0% to 7%, from 0% to 6%, from 0% to 5%, from 0% to 4%, from 0% to 3%, from 0% to 2%, from 0% to 1%, from 5% to 20%, from 5% to 19%, from 5% to 18%, from 5% to 17%, from 5% to 16%, from 5% to 15%, from 5% to 14%, from 5% to 13%, from 5% to 12%, from 05% to 11%, from 5% to 10%, from 5% to 9%, from 5% to 8%, or from 5% to 7%.

In various embodiments analytic results include compensation for or consideration of multi-analyte interference, relative differences in extraction recovery, and matrix factors.

In various embodiments, a method of the present invention has a lower limit of quantitation for one or more GAGs or components thereof of 10 μM or less, e.g., 9 μM, 8 μM, 7 μM, 6 μM, 5 μM, 4 μM, 3 μM, 2 μM, 1 μM, 0.9 μM, 0.8 μM, 0.7 μM, 0.6 μM, 0.5 μM, 0.4 μM, 0.3 μM, 0.2 μM, 0.1 μM, 0.05 μM, 0.01 μM or less.

In particular embodiments in which the level of HS measured in a sample is from 1 ng/mL to 10,000 ng/mL, e.g., 1 ng/mL, 2 ng/mL, 3 ng/mL, 4 ng/mL, 5 ng/mL, 10 ng/mL, 20 ng/mL, 30 ng/mL, 40 ng/mL, 50 ng/mL, 100 ng/mL, 500 ng/mL, 1000 ng/mL, 2000 ng/mL, 3000 ng/mL, 4000 ng/mL, 5000 ng/mL, 6000 ng/mL, 7000 ng/mL, 8000 ng/mL, 9000 ng/mL, or 1000 ng/mL, or any range therebetween, e.g., 200 ng/mL to 1000 ng/mL, 200 ng/mL to 5000 ng/mL, 1000 ng/mL to 5000 ng/mL, or 3000 ng/mL to 5000 ng/mL.

Biomarkers

In some instances, methods and compositions of the present invention are used to measure the level of one or more GAGs, components thereof (e.g., component disaccharides), or molecules derived therefrom in a subject, where the subject is also, has also been, or is subsequently measured for a second characteristic. In various instances, the second trait is a biomarker, e.g., a biomarker of a GAG-associated condition.

In some instances, a GAG-associated condition is characterized, monitored, or diagnosed according to one or more biomarkers as described herein or known in the art. A biomarker, e.g., a GAG condition biomarker (a biomarker associated with a GAG condition), can have a range or constellation of values. A GAG condition biomarker can have a GAG condition-associated value, range of values, constellation of values, or a GAG condition-associated relationship with patient or population normative or control values (e.g., where values above or below a certain standard value are considered to be associated with a GAG-associated condition). A GAG condition-associated biomarker can also have a non-GAG condition-associated value, range of values, constellation of values, or non-GAG condition-associated relationship with a patient or population normative or control values. In some instances, treatment of a GAG condition will encompass a change or trend in the temporal mean, mode, or moment-to-moment value of a biomarker from a GAG condition-associated value to or toward a non-GAG condition-associated value. Moreover, a biomarker may be measured in the course of determining disease progress and/or treatment progress or efficacy.

Biomarkers of one or more GAG conditions can include, without limitation, information obtained through imaging techniques, observation, cognitive testing, and the analysis of patient samples. For instance, a biomarker of a GAG condition can include one or more of a standardized neurocognitive assessment, a standardized behavioral assessment, Bayley Scales of Infant Development (e.g., BSID-III) results, Kaufmann Assessment Battery for Children (e.g., KABC-II) results, Sanfilippo-specific behavioral rating scale assessment results, Four Point Scoring System/Total Disability Score (FPSS/TDS) results, Sanfilippo Behavioral Rating Scale (SBRS) results, gross motor skill assessment results, fine motor skill assessment results, voluntary movement assessment results, Movement Assessment Battery for Children (e.g., MABC-2) results, functional adaptive behavior assessment results, Adaptive Behavior Composite (ABC) results, Vineland Adaptive Behavioral Scales results (e.g., VABS-II) results, quality of life (QoL) assessment results, CHILD HEALTH QUESTIONNAIRE™ results (e.g., Parent Form 50 (CHQ-50) results; e.g., Child Form 87 (CHQ-87) results), INFANT TODDLER QUALITY OF LIFE QUESITONNAIRE™ (ITQOL; e.g., ITQOL-97) results, Children's Sleep Habits Rating Scale results, Children's Sleep Habits Questionnaire (CSHQ) results, Mullens Scales of Early Learning (MSEL) results, Griffiths Scale of Mental Abilities results, Leiter Scales results, Stanford Binet Intelligence Scale results, Wechsler Preschool and Primary Scale of Intelligence results, Wechsler Adult Intelligence Scale (WAIS-IV) results, Differential Abilities Scale results (e.g., Differential Abilities Scale II; DASII) results, therapeutic concentration in CSF and/or serum (e.g., a GAG condition therapeutic) results, brain MRI results, brain ABR results, liver size (e.g., as measured by MRI) results, spleen size (e.g., as measured by MRI) results, disease progression, progression of CNS GAG-condition-associated phenotypes, gray matter volume, white matter volume, intracranial CS volume (e.g., ventricles plus additional CSF space), auditory brainstem response (ABR) or Auditory Brainstem Response Assessed Hearing, event-related potentials (ERP), echocardiography results, abdominal MRI results, measures of the activity of any of one or more sulfatases, measures of the activity of any of one or more enzymes known to participate in GAG degradation, results of testing for or level of auditory agnosia, results of testing for or any change in hearing (e.g., hearing problems or hearing-related pathology), level or progression of CNS pathology, sleep disturbance, increased activity, behavior problems, seizure-like behavior, perseverative chewing, unsuccessful bowel training, unsuccessful bladder training, brain atrophy, hydrocephalus, sever white matter lesions, adverse events, and any laboratory test known in the art, e.g., standard laboratory tests.

A biomarker can include a quantitative of qualitative measurement or assessment of incidence, type, or severity.

In certain embodiments, a biomarker can be measured by, without limitation, electrocardiograms, clinical laboratory testing of CSF chemistries, CSF cell counts, CSF inflammatory markers, serum chemistry, serum chemistry liver function tests, hematology, urinalysis, or measures of the presence of antibodies against any of one or more particular targets (e.g., a target that is a therapeutic agent) in one or more tissues (e.g., in blood).

A biomarker may be inclusive of information gathered at a single time point or multiple time or data points. A biomarker inclusive of information gathered at multiple time or data points may be utilized in a raw or analyzed form, or in a measure determined by the analysis of two or more data points (e.g., a mean, slope, or integrated value).

In various instances, a biomarker is an adverse event.

In various instances, a biomarker is the level of one or more GAGs or components thereof in a sample. In various instances, a biomarker is a measure of total GAGs, e.g., a thrombin activity assay, e.g., a thrombin activity assay in which samples preincubated with human heparin cofactor II (HC II) are subsequently incubated with a fixed amount of thrombin and a fixed concentration of chromogenic substrate S-2238 in assay buffer in order to provide a measurement of total GAG. In certain particularly exemplified thrombin activity assays, GAG in CSF samples can bind with HC II, which in turn accelerates thrombin inactivation. In such an assay, GAG concentrations reflective of the molecules measured by the assay can be calculated from a disaccharide calibration curve. Non-disaccharide GAG concentrations according to such an assay can also be determined by after treatment of the samples with chondroitinase B, which specifically cleaves disaccharides.

As provided herein, a biomarker can also be the level of a particular GAG or component thereof (e.g., a component disaccharide) or cleavage product thereof as may be detected according to any of one or more of the assays provided herein or that would otherwise be understood to be encompassed by the present invention by those of skill in the art.

Biomarkers may also include biomarkers such as DNA or mRNA diagnostic or generic sequencing results. For instance, insofar as certain DNA or mRNA sequences, e.g., genomic sequences, are associated with an increased risk of one or more GAG conditions or the status thereof, the presence or absence of any such sequence in the genome or transcriptome of an individual, or the presence or absence of any such constellation of sequences in the genome or transcriptome of an individual, can be incorporated into diagnostic or treatment strategies including, e.g., the formulation of therapeutic formulations or regimens.

A biomarker may be a combination of one or more biomarkers including any of the above-mentioned biomarkers or others known in the art, e.g., a "fingerprint" of disease.

In some instances, a biomarker can be a second degree biomarker, i.e., a biomarker of a biomarker.

In various instances, a biomarker can be a measure of the level of one or more GAGs, one or more components thereof, or one or more cleavage products thereof. For instance, in various embodiments, a biomarker can be total GAG. Methods of determining total GAG are known in the art. In some embodiments, a biomarker is an alternative method of measuring one or more GAGs, e.g., an alternative to a method of the present invention. In various embodiments, a biomarker is a level of GAG measured in a qualitatively different sample, e.g., a sample from a different tissue or bodily fluid, e.g., CSF, blood, or urine, or any of the various other particular sample sources as provided herein.

Other biomarkers are known in the art.

In various instances of the present invention, any of the biomarkers provided herein may be measured in connection with any of one or more of Hunter Syndrome, SanA, SanB, or any other GAG condition provided herein or otherwise known to those of skill in the art. In certain embodiments, the biomarker is measured in a sample derived from a subject having, diagnosed as having, at risk of having, or diagnosed as being at risk of having any of one or more of Hunter Syndrome, SanA, SanB, or any other GAG condition provided herein or otherwise known to those of skill in the art. In various embodiments of the present invention, such a subject can be a subject that has been treated with, is simultaneously treated, or is subsequently treated with a therapeutic agent, e.g., a therapeutic agent for the treatment of a condition with which the subject has been diagnosed or for which the subject has been diagnosed as being at risk. For instance, a subject may be treated with an Idursulfase therapeutic for the treatment of Hunter Syndrome. For instance, a subject may be treated with ELAPRASE® for the treatment of Hunter Syndrome. In other instances, a subject may be treated with one or more of PEGASYS®, TYSABRI®, or BIAXIN®, e.g., independent of or in conjunction with ELAPRASE®.

Any of one or more drugs known for use in the treatment of a GAG condition, including, e.g., ELAPRASE®, may be provided in variety of dosage forms, dosages, routes of administration, etc. For instance, a therapeutic as provided herein may be administered intrathecally, e.g., by injection into the intrathecal space through a subcutaneously implanted intrathecal drug delivery device (IDDD). In other instances, a therapeutic as provided herein may be instead or additionally administered by way of a lumbar puncture. In various embodiments, the introduction to the intrathecal space will occur over a span of minutes, e.g., two to five minutes. A wide variety of applicable therapeutics, formulations, and routes of administration are known to those of skill in the art.

Moreover, methods provided herein may be used in a method of correlating the level of one or more GAGs or components thereof or cleavage products thereof with one or more biomarkers provided herein or otherwise known in the art.

With respect to the measurement of any of one or more biomarkers provided herein or otherwise known in the art, values may be determined at a single time point, at two time points, or at multiple regularly scheduled or irregularly sampled time points over a period of time. For instances, samples may be derived from a subject or group of subjects or selected members of a group of equivalent subjects over a period of time ranging from 10 minutes to 2 years or more, e.g., 10 minutes, 30 minutes, 1 hour, 6 hours, 12 hours, 1 day, 1 week, 1 month, 3 months, 6 months, 1 year, 2 years, or longer, or any range therebetween, e.g., 1 month to 6 months, 6 months to 1 year, or 1 year to 2 years.

Subjects as used herein may be, e.g., an embryo, a fetus, a child, or an adult. A child may be, e.g., less than 1 year old, less than 2 years old, less than 3 years old, less than 4 years old, less than 5 years old, less than 6 years old, less than 7 years old, less than 8 years old, less than 9 years old, less than 10 years old, less than 15 years old, or less than 18 years old, or any age therebetween. An adult may be, e.g., more than 18 years old, more than 20 years old, more than 25 years old, more than 30 years old, more than 40 years old, more than 50 years old, more than 60 years old, more than 70 years old, more than 80 years old, or older, or any age therebetween, e.g., 18 to 25 years old, 25 to 30 years old, 30 to 35 years old, 35 to 40 years old, 40 to 50 years old, or 50 to 60 years old.

Applications

Various methods as provided herein for the measurement of the level of one or more GAGs (e.g., HS) or components thereof (e.g., component disaccharides) or cleavage products thereof in a subject can be useful, e.g., in monitoring various GAG conditions, determining the severity of patients having various GAG conditions, monitoring the response of various GAG conditions to treatment, or diagnosing various GAG conditions.

Treatments are in development for various GAG-related conditions. For instance, an important treatment for Hunter Syndrome is enzyme replacement therapy (ERT). For example, ERT for Hunter Syndrome can include administering replacement I2S enzyme to patients with Hunter Syndrome. ELAPRASE®, manufactured by Shire plc, is a purified recombinant form of I2S approved by the FDA as an enzyme replacement therapy for the treatment of Hunter Syndrome. In another example, Sanfilippo B disease can be treated by enzyme replacement therapy with recombinant Naglu proteins. Another GAG condition, SanA, can result from an aberrant catabolism of HS due to a mutation in the degradation enzyme heparan N-sulfatase (HNS). One treatment strategy for SanA patients is enzyme replacement therapy (ERT) aiming at substituting the deficient hydrolase by a recombinant form of heparan N-sulfatase (HNS). Other treatments for GAG conditions can include arylsulfatase replacement such as NAGLAZYME® (galsulfase; arylsulfatase b) or alpha-L-iduronidase replacement such as ALDURAZYME® (laronidase)

There exists a need for methods of diagnosing, monitoring, and evaluating the treatment of these and other conditions related to the levels of one or more GAGs. The present invention provides, among other things, such methods.

In various embodiments, the methods and compositions of the present invention are employed to determine the level of one or more GAGs in a sample, e.g., a biological sample, e.g., a clinical sample.

In certain instances, the present invention is used to determine the level of one or more GAGs in a sample derived from a patient having a condition related to GAG levels, such that the method is applicable in tracking the progress of the condition through the evaluating the level of one or more GAGs in at least two samples derived from the patient at different times.

In certain instances, the present invention is used to determine the level of one or more GAGs in a sample derived from a patient having a condition related to GAG levels and receiving a therapeutic treatment. In such instances, the present invention may be employed to determine efficacy of treatment by evaluating the level of one or more GAGs in at least two samples derived from the patient at different times, at least one of the samples being derived from the patient after the initiation of treatment.

In certain instances, the present invention is used to correlate the level of one or more GAGs with one or more additional biomarkers, e.g., a biomarker associated with a disease linked to GAG levels. For example, biomarker levels may be measured before or at the beginning of a treatment course (e.g., a baseline or control level). Biomarker levels may be measured at one or more time points throughout the course of treatment and compared with the level before the treatment or from an earlier time point of a treatment course. Identification or selection of appropriate treatment, determining if a patient has positive response to a treatment and/or optimization of the treatment can be guided using the information obtained in these methods.

Monitoring GAG Conditions

Methods of determining the level of one or more GAGs, one or more components thereof (e.g., component disaccharides), or one or more GAG cleavage products as provided herein may be utilized in monitoring GAG conditions, e.g., in monitoring the progression of or determining the severity of GAG conditions. For instance, samples may be derived from a particular subject or group of subjects on at least a first time point and a second, different time point (i.e., two or more distinct time points), and the level of one or more GAGs, one or more components thereof, or one or more GAG cleavage products can be determined from each sample by a method of the present invention. The change or trend between any of two or more distinct time points can provide an indication of the progression of a GAG condition. In one embodiment, an increase in the level of one or more GAGs, one or more components thereof, or one or more GAG cleavage products over time may be indicative of an increase in the severity of disease (i.e., progression toward greater severity). Alternatively, in another embodiment, a decrease in the level of one or more GAGs, one or more components thereof, or one or more GAG cleavage products over time may be indicative of a decrease in the severity of disease.

Those of skill in the art will appreciate that the efficacy of a method of monitoring the progress or determining the severity of a GAG condition will depend at least in part on the proper selection of a diagnostic GAG, GAG component, or GAG cleavage product. In various embodiments, as provided by the present invention, the level of a GAG can be calculated based on the measurement of GAG cleavage products, which provide a surrogate or proxy for direct measurement of the GAG. In other instances, the level of a GAG component or GAG cleavage product may be sufficiently diagnostic, e.g., insofar as the level of any one GAG component or GAG cleavage product is capable of informing to varying degrees the level of the GAG(s) from which it was derived or could have been derived.

Monitoring Treatment of GAG Conditions

Methods of determining the level of one or more GAGs, one or more components thereof, or one or more GAG cleavage products as provided herein may be utilized in monitoring the response of a GAG condition to treatment, e.g., in monitoring impact of a known or experimental treatment on the progression of a GAG condition in one or more subjects. For instance, samples may be derived from a particular subject or group of subjects that have received a treatment or serve as a control group for a treatment group (e.g., a non-treatment or placebo group). Samples may be taken from one or more of such groups in a manner consistent with accepted experimental practices on at least a first time point and a second, different time point (i.e., two or more distinct time points), and the level of one or more GAGs, one or more components thereof, or one or more GAG cleavage products can be determined from each sample by a method of the present invention. The change or trend between any of two or more distinct time points can provide an indication of the progression of a GAG condition, e.g., in the presence or absence of treatment. For instance, an increase, equal decrease, statistically indistinguishable change, or greater increase, in the level of one or more GAGs in one or more subjects, or in a group of subjects, receiving a treatment as compared to the same one or more GAGs in one or more subjects, or in a group of subjects, in a control group over time can be indicative of treatment inefficacy. Alternatively, a statistically significant decrease or lesser increase in the level of one or more GAGs in one or more subjects, or in a group of subjects, receiving a treatment as compared to the same one or more GAGs in one or more subjects, or in a group of subjects, in a control group over time can be indicative of treatment efficacy. In such embodiments, the treatment can be an experimental treatment.

In other embodiments, methods of the present invention are used to provide data indicative of the effect of treatment, e.g., a known treatment, in an individual or group of individuals. For instance, samples may be derived from a particular subject on at least a first time point and a second, different time point (i.e., two or more distinct time points), and the level of one or more GAGs, one or more components thereof, or one or more GAG cleavage products can be determined from each sample by a method of the present invention. The change or trend between any of two or more distinct time points can provide an indication of the progression of a GAG condition. Comparison of the trend in the progression of the condition may be indicative of treatment efficacy in the subject. For instance, an increase in the level of a relevant GAG can be indicative of ineffective treatment.

A decrease in the level of a relevant GAG can be indicative of effective treatment. In other circumstances, e.g., where treatment decreases the rate at which GAG levels rise and slows the rate of GAG condition progression (even if the absolute trend is an increase in GAG levels), results may be indicative effective treatment.

In one embodiment, those of skill in the art will appreciate that the efficacy of a method of monitoring the progress or determining the severity of a GAG condition will depend, at least in part, on the proper selection of a diagnostic GAG, GAG component, or GAG cleavage product. In various embodiments, as provided by the present invention, the level of a GAG can be calculated based on the measurement of GAG cleavage products, which provide a surrogate or proxy for direct measurement of the GAG. In other instances, the level of a GAG component or GAG cleavage product may be sufficiently diagnostic, e.g., insofar as the level of any one GAG component or GAG cleavage product is capable of informing to varying degrees the level of the GAG(s) from which it was derived or could have been derived.

In some embodiments, inventive methods described herein can be used for monitoring treatment response in a Sanfilippo syndrome or Hunter syndrome patient. Typically, for example, the levels of one or more biomarkers in a Sanfilippo syndrome of Hunter syndrome patient are measured after receiving treatment for the disease. The measured levels are then compared to a control level to determine if the patient has positive response to the treatment. As used herein, a "positive response" to a treatment includes reduced severity of disease symptoms, slowed progression, abatement or cure of the disease. A suitable control level may be the level of the one or more biomarkers obtained from the same patient before receiving the treatment (e.g., baseline) or measured at an earlier time point of the treatment. In some embodiments, a suitable control level is the level of the one or more biomarkers in a control Sanfilippo syndrome or Hunter syndrome patient without the treatment. In some embodiments, such a control level may be determined from a significant number of control patients, and an average or mean is obtained. Typically, a control patient is at a comparable disease or developmental stage. Typically, a diminished or elevated level with statistical significance of the one or more biomarkers as compared to a suitable control level indicates that the patient has positive response to the treatment. Various statistical methods and techniques such as those described herein may be used to determine statistical significance. In some embodiments, a biomarker has a diminished level if the level of the biomarker measured in a biological sample obtained at a relevant time point of interest is reduced by more than 10%, 20%, 30%, 40%, 50%, 60%, 70%, 80%, 90%, 95% as compared to a control level. In some embodiments, a biomarker has an elevated level if the level of the biomarker measured in biological samples is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold higher as compared to a control level.

Inventive methods of the present invention may be applied to all types of Sanfilippo syndrome (e.g., Sanfilippo syndrome Type A, B, C, and D), Hunter syndrome and various treatment for either disease. In particular, inventive methods described herein may be used to identify enzyme replacement therapy as a proper treatment for Sanfilippo syndrome of Hunter syndrome. Using Sanfilippo syndrome Type A as a non-limiting example, a physician may recommend administering a recombinant heparan N-sulfatase (HNS) protein as treatment to a patient based on the level of one or more biomarkers determined using methods described herein. For example, a physician may determine a therapeutically effective amount of the therapeutic agents (e.g., replacement enzymes such as HNS proteins), administration intervals and/or routes, at least in part based on the biomarker levels according to the present invention. Using Hunter syndrome as a non-limiting example, a physician may recommend administering a recombinant iduronate-2-sulfatase (I2S) protein as treatment to a patient based on the level of one or more biomarkers determined using methods described herein. For example, a physician may determine a therapeutically effective amount of the therapeutic agents (e.g., replacement enzymes such as iduronate-2-sulfatase protein), administration intervals and/or routes, at least in part based on the biomarker levels according to the present invention.

In certain instances, the present invention includes a method of monitoring treatment of a lysosomal storage disease, in which method a patient suffering from the lysosomal storage disease is treated by administration of a replacement enzyme, e.g., in a therapeutically effective dose. Such treatment can be accompanied by measurement at one or more points in time of the level of one or more glycosaminoglycans according to any method thereof, such as any method provided herein. The level of glycosaminoglycan can be measured from any biological sample obtained from the patient, including any sample tissue as described herein. In particular instances, the sample can be representative of a point in time that is before, during, or after a treatment or course of treatment for the lysosomal storage disease.

Examples of such lysosomal storage diseases include, for example, MPSI, MPSII, MPSIIIA, MPSIIIB, MPSIIIC, MPSIIID, MPSIVA, MPSIVB, MPSVI, MPSVII, MPSIX, alpha mannosidosis, aspartylglucosaminuria, Fabry, fucosidosis, galactosialidosis, Gaucher disease, GM1 gangliosidosis, GM2 activator deficiency, sialidosis, Krabbe, metchromatic leukodystrophy, mucolipidosis IV, multiple sulfatase deficiency, Pompe, Sandhoff, Tay-Sachs, AB Variant Schindler Disease, Salla Disease, beta mannosidosis, and globoid cell leukodystrophy.

A replacement enzyme administered to treat a lysosomal storage disorder can be, for example, a recombinant enzyme, such as, in one particular example, a recombinant human heparan N-sulfatase or recombinant idursulfase.

The treatment administered to a patient having a lysosomal storage disease can include administration of a lysosomal replacement enzyme at any dosage, such as a therapeutically effective dose and/or a dose selected from 1 mg to 500 mg, such as 1 mg, 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 200 mg, 300 mg, 400 mg, or 500 mg or more.

Administration of a therapeutic for treatment of a lysosomal storage disease, e.g., a replacement enzyme for treatment of a lysosomal storage disease, can occur at any interval. Exemplary intervals of administration include daily, weekly, biweekly, monthly, bimonthly, yearly intervals, or as needed, as well as at any combination thereof. Thus, doses may be repeated, e.g., weekly, monthly, or at other time intervals, or as needed.

Glycosaminoglycan levels may be measured in any of a variety of biological samples including any sample as described herein. Exemplary tissues include, e.g., cerebrospinal fluid (CSF), whole blood, cells, tissue, plasma, serum, blood, urine and combinations thereof.

In various embodiments, the results of a monitoring or measurement of glycosaminoglycan levels can impact the course of treatment (e.g., the administration dose or administration interval). For example, if a glycosaminoglycan level is measured to be reduced as compared to a control glycosaminoglycan level, administration dose and/or administration interval may be maintained. More specifically, in certain instances, if a glycosaminoglycan level is measured to be reduced, e.g., at least 10%, at least 20%, at least 30%, at least 40%, at least 50%, at least 60%, at least 70%, at least 80%, at least 90% or more as compared to a control glycosaminoglycan level, administration dose and/or administration interval may be maintained.

In some examples, if a glycosaminoglycan level is measured to be reduced as compared to a control glycosaminoglycan level, administration dose and/or administration interval may be adjusted. In various such embodiments, the GAG level is reduced by 1% or less, 2% or less, 3% or less, 4% or less, 5% or less, 6% or less, 7% or less, 8% or less, 9% or less or 10% or less as compared to a control glycosaminoglycan level. In some examples, if a glycosaminoglycan level is measured to be reduced as compared to a control glycosaminoglycan level, administration dose may be increased (e.g., by 5%, 10%, 20%, 30%, 40%, 50%, 75%, 2-fold, 3-fold, 4-fold, 5-fold, or 10-fold or more). In some examples, if a glycosaminoglycan level is measured to be reduced as compared to a control glycosaminoglycan level, administration dose may be decreased (e.g., by 5%, 10%, 20%, 30%, 40%, 50%, 75%, 2-fold, 3-fold, 4-fold, 5-fold, or 10-fold or more). In some examples, if a glycosaminoglycan level is measured to be reduced as compared to a control glycosaminoglycan level, administration interval may be decreased (e.g., by 5%, 10%, 20%, 30%, 40%, 50%, 75%, 2-fold, 3-fold, 4-fold, 5-fold, or 10-fold or more). In some examples, if a glycosaminoglycan level is measured to be reduced as compared to a control glycosaminoglycan level, administration interval may be increased (e.g., by 5%, 10%, 20%, 30%, 40%, 50%, 75%, 2-fold, 3-fold, 4-fold, 5-fold, or 10-fold or more).

In some examples, if a glycosaminoglycan level is measured to be increased (e.g., by 5%, 10%, 20%, 30%, 40%, 50%, 75%, 2-fold, 3-fold, 4-fold, 5-fold, or 10-fold or more) as compared to a control glycosaminoglycan level, administration dose and/or administration interval may be adjusted. In various such embodiments, the GAG level is increased by at least 1%, at least 10%, at least 20%, at least 30%, at least 40%, at least 50%, at least 60%, at least 70%, at least 80%, at least 90% or more. In some examples, if a glycosaminoglycan level is measured to be increased as compared to a control glycosaminoglycan level, administration dose may be increased (e.g., by 5%, 10%, 20%, 30%, 40%, 50%, 75%, 2-fold, 3-fold, 4-fold, 5-fold, or 10-fold or more). In some examples, if a glycosaminoglycan level is measured to be increased as compared to a control glycosaminoglycan level, administration dose may be decreased (e.g., by 5%, 10%, 20%, 30%, 40%, 50%, 75%, 2-fold, 3-fold, 4-fold, 5-fold, or 10-fold or more). In some examples, if a glycosaminoglycan level is measured to be increased as compared to a control glycosaminoglycan level, administration interval may be decreased (e.g., by 5%, 10%, 20%, 30%, 40%, 50%, 75%, 2-fold, 3-fold, 4-fold, 5-fold, or 10-fold or more). In some examples, if a glycosaminoglycan level is measured to be increased as compared to a control glycosaminoglycan level, administration interval may be increased (e.g., by 5%, 10%, 20%, 30%, 40%, 50%, 75%, 2-fold, 3-fold, 4-fold, 5-fold, or 10-fold or more).

In various embodiments, a control GAG level can be, e.g., a GAG level in the subject suffering from the lysosomal storage disease, a GAG level in the subject suffering from the lysosomal storage disease measured at an earlier time point during treatment, or a GAG level in an untreated control subject.

Diagnosing GAG Conditions

Methods of determining the level of one or more GAGs, one or more components thereof (e.g., component disaccharides), or one or more GAG cleavage products as provided herein may be utilized in diagnosing GAG conditions, e.g., in determining whether a subject presents a GAG level that is likely indicative of a pathological state. GAGs include, e.g., hyaluronan, keratan sulfate (KS), chondroitin sulfate (CS), dermatan sulfate (DS), heparan sulfate (HS), heparin, chondroitin sulfate/dermatan sulfate (CS/DS), and heparan sulfate (HS)/heparin. Determination of a pathological GAG level may include monitoring GAG levels over a period of time and identifying any trend in GAG levels over the monitored period. Determination of a pathological GAG level may include measuring the level of one or more GAGs at one or more than one time points and comparing the measured level to an established standard value. A standard value may be established, e.g., with respect to a method provided herein by sampling statistically significant numbers of subjects having a given GAG condition and subjects not having a GAG condition and comparing, inspecting, or manipulating the values derived therefrom.

Those of skill in the art will appreciate that the efficacy of a method of monitoring the progress or determining the severity of a GAG condition will depend at least in part on the proper selection of a diagnostic GAG, GAG component, or GAG cleavage product. In various embodiments, as provided by the present invention, the level of a GAG can be calculated based on the measurement of GAG cleavage products, which provide a surrogate or proxy for direct measurement of the GAG. In other instances, the level of a GAG component or GAG cleavage product may be sufficiently diagnostic, e.g., insofar as the level of any one GAG component or GAG cleavage product is capable of informing to varying degrees the level of the GAG(s) from which it was derived or could have been derived.

Treatment Regimen Determination

Using methods described herein, medical practitioners may select and prescribe treatments adapted to each individual patient based on the diagnosis and disease staging provided to the patient through determination of the expression and/or activity levels of one or more biomarkers described herein (e.g., biomarkers for Sanfilippo syndrome of Hunter syndrome such as GAG). Selection of an appropriate therapeutic regimen for a given patient may be made based solely on the diagnosis/staging provided by inventive methods described herein. Alternatively or additionally, a medical practitioner may also consider other clinical or pathological parameters used in existing methods to diagnose Sanfilippo syndrome or Hunter syndrome and assess the advancement of the disease.

The doses and frequencies of the treatment may be adjusted to optimize the therapeutic efficacy. Suitable samples for monitoring treatment response may include, but are not limited to, cerebrospinal fluid (CSF), cells, tissue, whole blood (e.g., peripheral blood sample), plasma, serum, blood, urine and combination thereof. Additional biological samples described above may also be used.

As will be understood from the present specification, the present invention includes a variety of embodiments in which GAGs are digested into cleavage products, which are quantified such that the quantification of the cleavage products, e.g., by mass spectrometry, provides a measure of the level of the GAG from which the cleavage products are derived. This value can be used in various applications as provided herein. Various methods of the present invention can include, without limitation with respect to number, repetition, exclusion of particular steps, or order of particular steps, extraction, desalting, digestion, derivatization, optional glycan-specific extraction, separation, and detection.

EXAMPLES

The examples described herein demonstrate the use of mass spectrometry to determine the level of glycosaminoglycans. The present invention is based, in part, on the below examples, which demonstrate the utility of mass spectrometry methods for determining the level of glycosaminoglycans.

In at least some examples, a method is described in which a 50 µl sample of cerebrospinal fluid was analyzed in a procedure including ion exchange solid-phase extraction of heparan sulfate, size exclusion desalting, digestion with heparinases, chemical derivatization of the resulting disaccharides, and solid-phase extraction. In at least some examples, six heparan sulfate disaccharides identified as I-S, II-S, III-S, IV-S, II-A, and IV-A were derivatized with 4-Butylaniline. In certain examples, quantification of analytes was performed using liquid chromatography (LC), e.g., reverse-phase liquid chromatography, followed by mass spectrometry (MS).

Example 1: Liquid Chromatography/Mass Spectrometry (LC/MS) Assay for Quantification of Heparan Sulfate in Cerebrospinal Fluid of Mucopolysaccharidosis Patients Heparan sulfate was quantified in a human cerebrospinal fluid sample by a method in which disaccharides derived from the heparan sulfate in the sample were quantified using a multistep procedure. In particular, the multistep procedure of the present example included ion exchange solid-phase extraction, size exclusion desalting, digestion with heparinase, chemical derivatization, and glycan-specific solid-phase extraction. Subsequent to glycan-specific solid-phase extraction, the disaccharides were analyzed by liquid chromatography in conjunction with tandem mass spectrometry using an API 5000™ triple quadruple mass spectrometer operating in the electrospray negative ion mode.

Extraction of HS from CSF

Diethylaminoethyl (DEAE) resin (175 µL) was added to the wells of a 96 well plate with 20 µm frit. The resin was equilibrated by addition of 300 µL of loading/wash buffer (20 mM Tris-HCl, 0.1 M NaCl, pH 7.4) and centrifugation for one minute at 50 RCF. CSF (50 µL) was combined with 175 µL loading/wash buffer, loaded on the resin and centrifuged. The wells were washed twice with 300 µl of loading/wash buffer and HS was eluted from the resin into a collection plate using 140 µL, of elution buffer (20 mM Tris-HCl, 1 M NaCl, pH 7.4). The eluates were desalted using G-25 gel filtration Multitrap plates according to manufacturer protocol and dried by centrifugal evaporation.

Digestion of HS into Disaccharides

HS in each extracted well was dissolved in 50 µL heparinase digestion buffer (25 mM ammonium acetate, 1 mM calcium acetate, pH 7.0). Digestion into constituent disaccharides was performed using 12 U heparinase I, 4 U heparinase II and 1.4 U heparinase III. The reaction was let to proceed overnight at 30° C. and then dried by centrifugal evaporation in preparation for subsequent labeling of the disaccharides.

Labeling and Clean-Up of Disaccharides

HS includes a linear polymer made of repeating disaccharide subunits constituted of a hexuronic acid (HexA) α/β1-4 glucosamine (GlcN) α4 backbone. Disaccharide backbone can be modified biosynthetically by different chemical groups. For instance, a HexA unit can be sulfated on the 2-O position and the carboxyl group can be epimerized into two opposite orientations with regards to the plane of the ring. GlcN can occur sulfated on its 6 and more rarely 3 hydroxyl oxygens. The amine nitrogen is very rarely free and is more frequently substituted by either sulfation or acetylation. Owing at least in part to such heterogeneities, HS chains are very difficult to analyze. Analysis and quantification of the constituent disaccharides contributes to a solution to this difficulty. Labeling of disaccharides is a step that, in at least some of the present methods, can further contribute to the utility of such methods, as is further described below.

Disaccharides were quantified as surrogates for parent polymer by enzymatically depolymerizing HS using bacterial heparinases I, II and III. The enzymes cut the linkage between the disaccharides generating various cleavage products, of which at least eight isoforms were commonly detected (FIG. 1). Many of the released disaccharides such as IIS/IIIS and IIA/IIIA are isomeric and therefore are detected at the same mass-to-charge ratio (m/z) by mass spectrometry. Therefore, in the present Example, in order to be able to quantify these disaccharides individually, it is important to separate them in the chromatographic dimension prior to mass spectrometric detection.

Figure 2A:
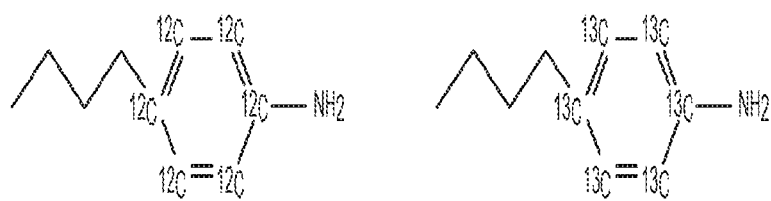
FIGS. 2A and 2B are exemplary diagrams and a graph depicting reductive amination of HS disaccharides with 4-butylaniline (4-NBA).

Modification of hydrophilic disaccharides by reductive amination with a hydrophobic label improves or makes possible their separation by RP chromatography. 4-butylaniline (4-NBA) was a promising labeling candidate due its hydrophobicity, commercial availability in a deuterated form and the ease of its organic synthesis in large quantities in a $^{13}C$ version (FIG. 2A).

HS disaccharides were labeled with $^{12}C$-4-NBA by reductive amination. The reaction was performed by addition of 13 µL of a 0.57 M sodium cyanoborohydride solution dissolved in 7:3 (v/v) dimethyl sulfoxide (DMSO):glacial acetic acid solution and 2 µL 4-NBA to each well of dried disaccharides. The plate was incubated at 37° C. with intermittent shaking for 2 hours. The labeling reaction was diluted in 200 µL 98:2 acetonitrile:water containing 0.58 µM of disaccharide mixture previously derivatized with $^{13}C$-labeled 4-NBA to act as an internal standard ($I_{std}$). The molar composition of the $I_{std}$ mixture is identical to that of the calibrators used for the calibration curve (see below). The solution containing labeled disaccharides and their $I_{std}$ was purified from the labeling reaction excess reagents by solid-phase extraction (SPE). For this purpose, GlykoClean S-Plus HILIC cartridges (Prozyme, Hayward, Calif.) in a 96 well format were used according to manufacturer vacuum protocol. In brief, the resin was primed with 1 mL of water followed by equilibration with 1 mL of acetonitrile. The 200 µL of labeled disaccharides in 98:2 acetonitrile:water containing $I_{std}$ were loaded on the resin, washed with 500 µL of acetonitrile followed by elution with 500 µL of pure water. To the eluates, 10 µL of tributylamine (0.5% in acetonitrile) was added and samples were directly analyzed by LC/MS.

LC/MS

HS disaccharides were separated by Reversed-phase (RP) chromatography with online mass spectrometric detection. The column used was HSS T3RP18 (1.7 μm, 2.1×100 mm) (Waters, Milford, Mass.) operated on a Waters Acquity with a flow rate of 0.3 ml/min and a column temperature of 25° C. The mobile phase A was 60 mM ammonium acetate pH 5.4 whereas mobile phase B was acetonitrile. The gradient included an initial 1 minutes equilibration at 98% A, followed by a decrease to 60% A over a period of 8 minutes to elute the disaccharides. The column was washed with 20% A for 1 minute prior to re-equilibration with 98% A for 1 minute. The total run time was 12 minutes.

Mass spectrometric detection was conducted using an API 5000 mass spectrometer (AB Sciex, Concord, Ontario) equipped with a triple quadrupole analyzer operated in the negative polarity, multiple reaction monitoring mode. The source was tuned for detection of disaccharides under the following conditions: curtain gas 20, GS1 50, GS2 50, and transfer capillary temperature of 450° C. The transitions used to detect the $^{12}$C-4-NBA labeled disaccharides were as follows: ΔUA,2S-GlcNS,6S (I-S or IS)(709.1/549.2), ΔUA-GlcNS,6S (II-S or IIS)(629.1/549.2), ΔUA,2S-GlcNS (III-S or IIIS)(629.1/549.2), ΔUA-GlcNS (IV-S or IVS)(549.2/391.2), ΔUA-GlcNAc,6S (II-A or IIA)(591.2/433.2) and ΔUA-GlcNAc (IV-A or IVA) (511.2/157.0). The transitions used for the detection of the $^{13}$C-4-NBA labeled $I_{std}$ disaccharides were the following: IS (715.1/555.2), IIS (635.1/555.2), IIIS (635.1/555.2), IVS (555.2/397.2), IIA (597.2/439.2), and IVA (517.2/157.0)

Construction of Calibration Curve

To generate the calibrants, six commercially obtained disaccharides that are most abundant in human CSF namely, IS, IIS, IIIS, IVS, IIA, and IVA, were mixed together in the following respective molar percent ratios: 10%, 5%, 15%, 10%, 10% and 50%. Eight non-zero calibrants were used with increasing total disaccharide concentration levels (0.1 μM, 0.25 μM, 0.8 μM, 2.5 μM, 6.0 μM, 17.5 μM, 40 μM, and 50 μM). The lower-limit of quantification and the upper-limit of quantification were respectively 0.1 μM and 50 μM. Each level was spiked into 50 μL CSF that has already undergone DEAE extraction and desalting. Heparinase addition to the matrix was omitted in order to avoid digestion of endogenous HS. The calibrator mixture was labeled with $^{12}$C-4-NBA and purified by SPE in the presence of $I_{std}$ as described above. The sum of normalized intensities of the six $^{12}$C disaccharides to their respective $^{13}$C $I_{std}$ was plotted as a function of the total disaccharide concentrations of the calibrators. The best-fit linear regression model with $1/x^2$ weighing was used to generate the calibration curve.

Validation Tests

For the preparation of disaccharide quality controls (DS QC), disaccharide mixtures mimicking the calibrators were prepared at the lower limit of quantification (LLOQ) and higher concentration levels spanning the calibration curve range (0.3 μM, 2 μM, 15 μM and 37.5 μM). The QCs were quantified based on the calibration curve. Accuracy (% bias) and precision (% CV; n=6) were determined.

To prepare HS quality controls (HS QCs), the disaccharide equivalent of a highly concentrated 2 mg/ml bovine kidney HS stock solution was determined based on a disaccharide calibration curve. Low, low-mid, mid and high HS QCs were prepared from the stock with spike-in concentrations of 0.3 μM, 2.0 μM, 15.0 μM and 37.5 μM. The nominal disaccharide concentrations of the HS QC were calculated by adding the disaccharide contribution of the endogenous HS from the matrix lot used to the spike-in disaccharide concentrations. The HS QCs were run through the entire sample preparation protocol and the accuracy and precision (n=6) were calculated.

To test the ability to dilute samples that fall above the upper limit of quantification (ULOQ), a highly concentrated HS QC (400 μM; n=6) was quantified after dilution with blank matrix to a quantifiable level within the calibration curve range. Accuracy and precision were determined.

To assess matrix effects, DS QCs at low and high levels were spiked into six different lots of extracted/desalted matrix then labeled and purified. The average, mass spectrometric response was compared to that of disaccharides injected and processed at the same concentration in neat solution. The matrix factor (MF) is the ratio of the average signal in matrix to that in neat solution.

To gauge the extent of carryover following runs of highly concentrated samples, blanks were injected after the highest concentration calibrators and evaluated for the presence of analytes.

Selectivity can refer to the ability of the assay to detect the desired analytes without interference from other matrix components. To test the assay selectivity, six different lots of blank matrix were evaluated for interfering peaks at the same transition and retention time as HS disaccharides. Because HS is endogenous, only undigested matrix is used.

The interference of $I_{std}$ to analyte was evaluated by spiking $I_{std}$ in matrix at the concentration used in the assay and monitoring signals at the characteristic transitions and retention times of the analytes.

The reinjection reproducibility of processed samples was determined by reinjecting previously acceptable calibration standards and quality control samples that had been stored under specified test conditions. The quality control concentrations were calculated from the reinjected calibration curve and were compared against theoretical values.

The extract stability of processed samples was determined by reinjection of previously acceptable quality control samples that were stored under specified test conditions along with a freshly extracted standard curve and analytical quality control samples. The quality control concentrations were calculated from the freshly extracted calibration curve and were compared against theoretical values.

The matrix stability was evaluated in several specific aspects, including freeze-thaw stability, bench top stability, and intermediate stability.

The solution stability was determined by comparing the response obtained from a solution stored under the test conditions (e.g., temperature, light exposure, etc.) to the response obtained from an aliquot of the same solution (control) that was not subjected to the test conditions. Long-term solution stability was determined by comparing the response obtained from freshly prepared solutions (control) to the response obtained from a solution maintained at test conditions (e.g., reduced temperature, protected from light).

Chemical Labeling of HS Disaccharides with Heavy 4-NBA

Figure 2B:
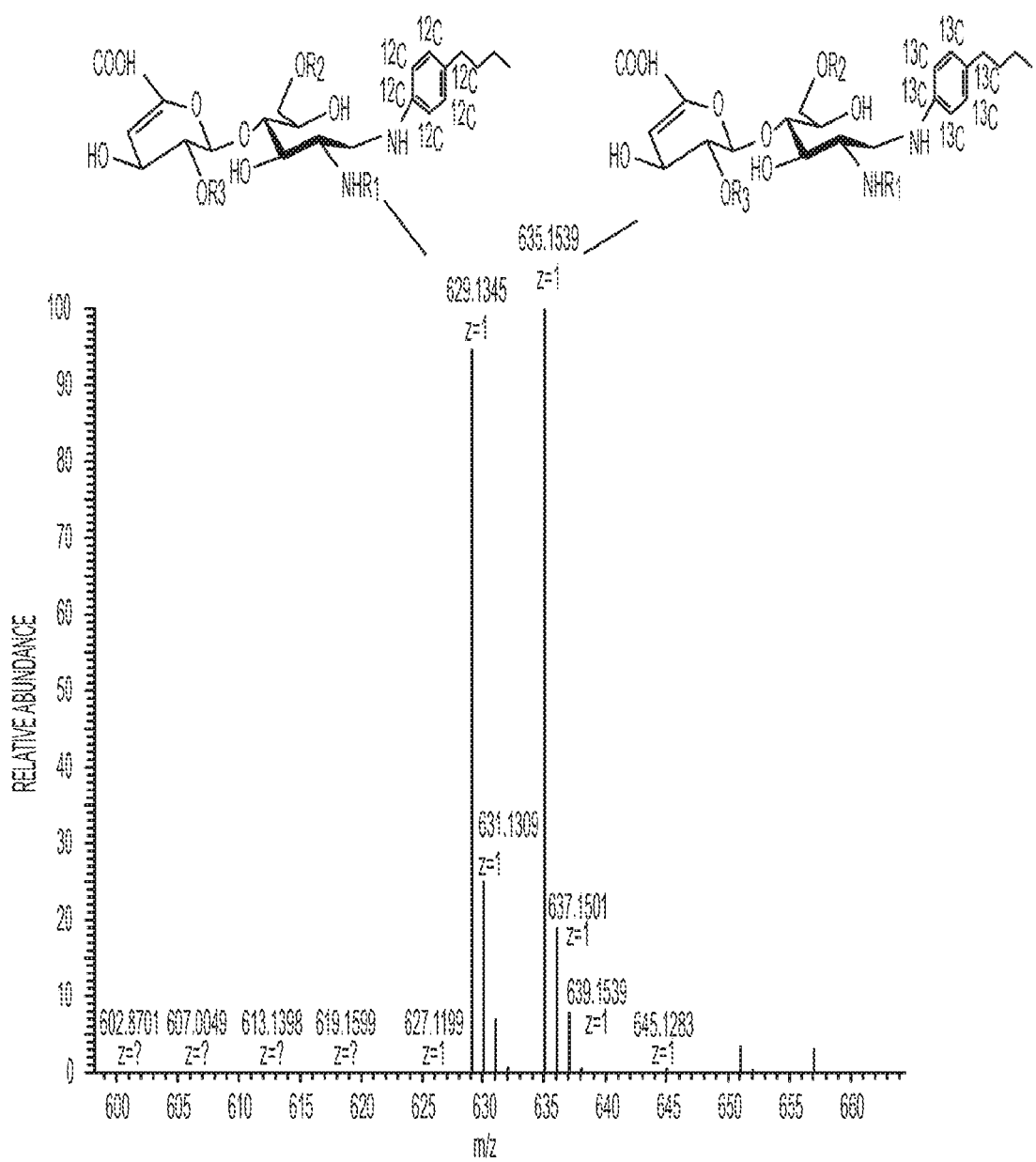

The isotopically labeled version of this label was desirable because it offered the possibility of generating $I_{std}$ for the monitored disaccharides. Introduction of $I_{std}$ during sample preparation and LC/MS analysis was crucial as it offset experimental variability thus enhancing the precision and accuracy of quantification. A commercially available version of 4-NBA is deuterated on the butyl hydrocarbon tail that interacts with the reversed-phase resin. This caused a slight, half-minute shift in retention times of the deuterated disaccharides during LC separation with respect to those labeled with the hydrogenated label. To circumvent this problem, a $^{13}$C-4-NBA labeled on the aniline ring was synthesized (FIG. 2A). Disaccharides labeled with this version co-eluted with their $^{12}$C counterparts while exhibiting a 6 Daltons shift in their m/z when singly charged during mass spectrometric detection (FIG. 2B). Hence, $^{13}$C-4-NBA labeled disaccharides were the analytes of choice to serve as $I_{std}$ in the present Example.

Reverse Phase Separation of Disaccharides

Figure 3:
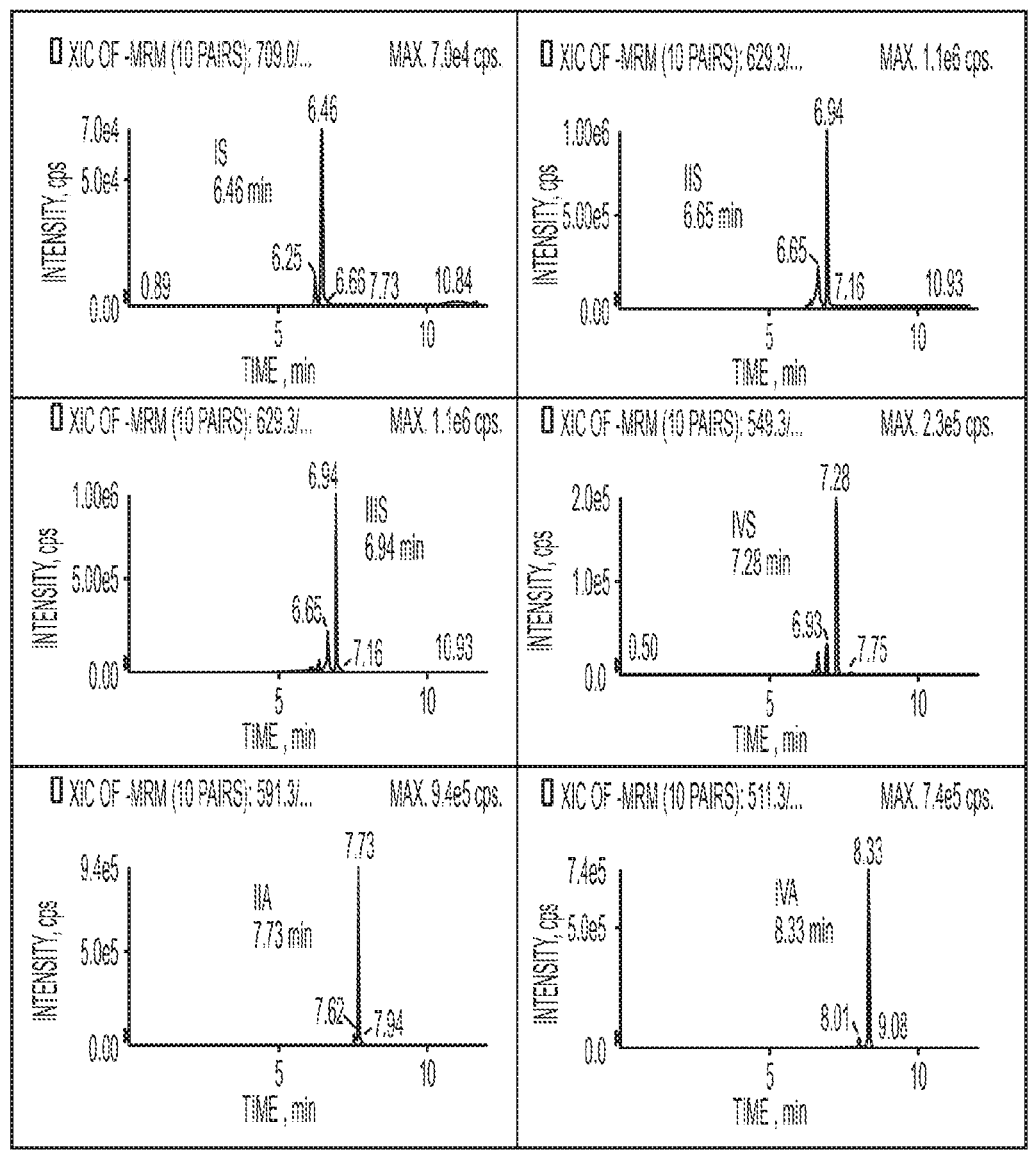
FIG. 3 is a series of exemplary graphs depicting LC/MS separation of 4-NBA labeled HS disaccharides using C18 reversed-phase chromatography. Six commercially available disaccharides representing abundant species generated from the digestion of HS in CSF of Sanfilippo syndrome A patients are shown. Separation was achieved by a short LC method of twelve minutes. The isomeric N-sulfated disaccharides IIS and IIIS are baseline resolved. Similarly, the N-acetylated isomers IIA and IIIA can be separated using this platform (not shown).

The covalent linkage of 4-NBA to HS disaccharides attenuates their hydrophilic character and makes them amenable to separation by RP C18 liquid chromatography. FIG. 3 shows the separation of six commercial HS disaccharide standards that represent abundant disaccharides generated from human CSF HS. The twelve minute LC/MS method increases sample turnover during analysis of large sample sets. The six disaccharides were resolved and eluted in increasing order of hydrophobicity. The triply sulfated disaccharide (IS) was the first to elute at 6.46 minutes while the unsulfated/acetylated one (IVA) has the strongest interaction with the resin and thus the longest retention time of 8.33 minutes. The Isomeric disaccharides IIS and IIIS with identical m/z were baseline resolved and eluted at 6.65 and 6.94 minutes respectively which facilitated their individual detection and quantitation. Similarly, the IIA/IIIA pair of isomers were resolved by this chromatography however, since IIIA is a minor component of human HS in CSF, it was disregarded from the analysis. In summary, the LC/MS platform described here has the power of separating HS disaccharides including isomers, using a short gradient which increases the throughput of sample analysis. Those of skill in the art will appreciate that elution characteristics may vary with variations in methodology.

Sample Preparation Protocol

Figure 4:
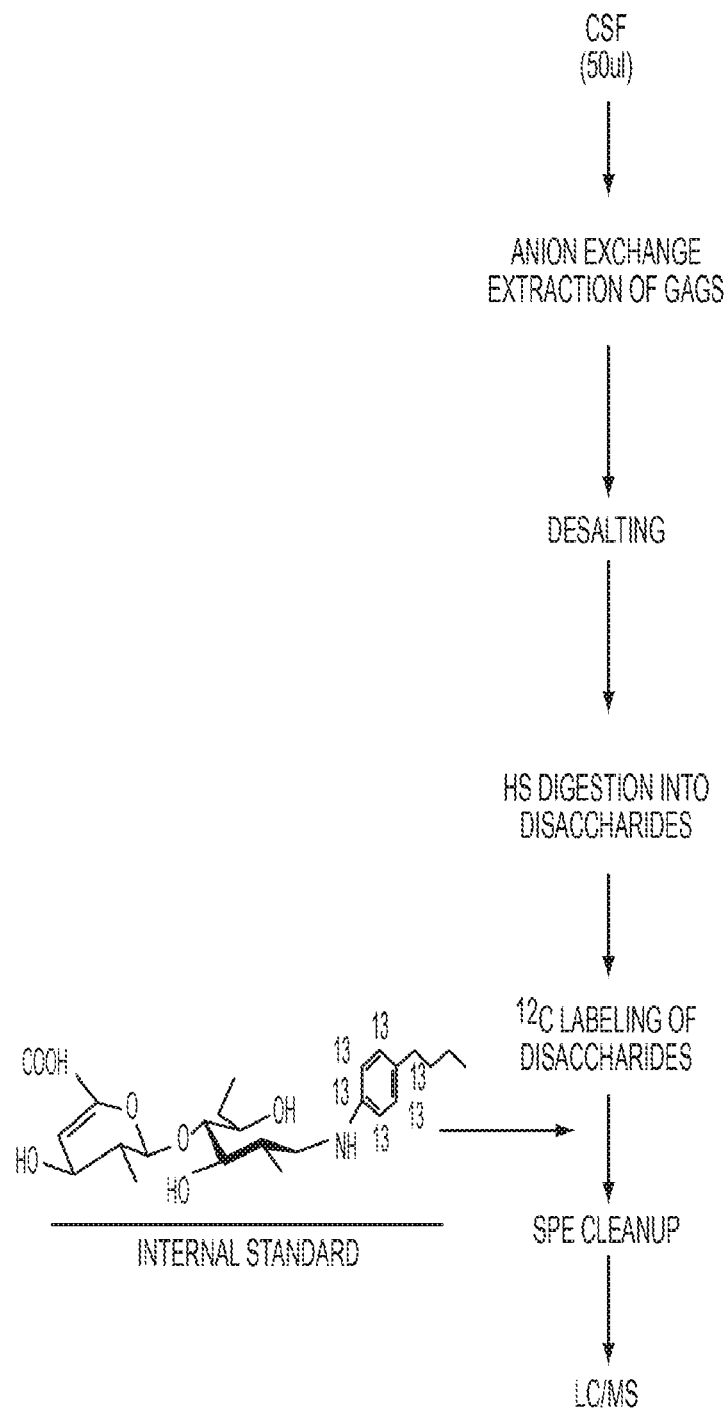
FIG. 4 is an exemplary diagram depicting steps of sample preparation procedure.

The CSF sample processing protocol took place in a 96-well plate format, a feature that provides utility during high-throughput sample analysis (FIG. 4). It was initiated by the extraction of the negatively charged GAGs by weak anion-exchange. The analytes that were retained on the resin were eluted with a high salt buffer and the eluate was then desalted using gel filtration cartridges. The HS fraction of the extract was depolymerized into its disaccharides building blocks using an HS-specific enzymatic cocktail containing heparinases I, II and III. The resultant disaccharides were reductively aminated by $^{12}$C-4-NBA and purified from excess labeling reagents that interfere with the downstream chromatography using hydrophilic interaction liquid chromatography (HILIC) solid phase extraction (SPE) plates. HS disaccharides were eluted with water and were readily analyzed by RP LC/MS. A mixture of disaccharides previously labeled with $^{13}$C-4-NBA, spiked into the samples as $I_{std}$ after the labeling step, served to offset sample-to-sample experimental variations that occurred in the downstream steps (FIG. 4). The multi-step assay protocol was validated extensively. Certain validation results are summarized in Table 1.

TABLE 1

Summary of validation tests.

| Validation test | Results |
| --- | --- |
| Linearity/accuracy of calibration curves | $R^2$ 0.9827-0.9950<br>% Bias −6.4% to 6.0% |
| Accuracy/Precision of disaccharide QCs (DS QCs) | Inter-assay accuracy (% Bias) −15.7% to 16.0%<br>Inter-assay Precision (% CV) 2.2% to 16.0% |

TABLE 1-continued

Summary of validation tests.

| Validation test | Results |
| --- | --- |
| Accuracy/Precision of HS QCs | Inter-assay accuracy (% Bias) −12.8% to 7.9%<br>Inter-assay Precision (% CV) 4.6% to 18.3% |
| Analyte Recovery | R(Low) 58.3%<br>R(Mid-Low) 45.4%<br>R(Mid) 43.8%<br>R(High) 47.3% |
| Accuracy/Precision of dilution QCs | % Bias = −0.8%<br>% CV = 7.8% |
| Matrix effects | MF (Low) = 0.789<br>MF (High) = 0.970 |
| Analyte carryover | Carryover was observed only in three analytical runs with a peak area ratio >25% of the lowest calibrator |
| Selectivity | The method is selective in undigested matrix |
| Interference of $I_{std}$ to analyte | No significant interference found |

Linearity and Accuracy of the Best-Fit Calibration Curve

Figure 5:
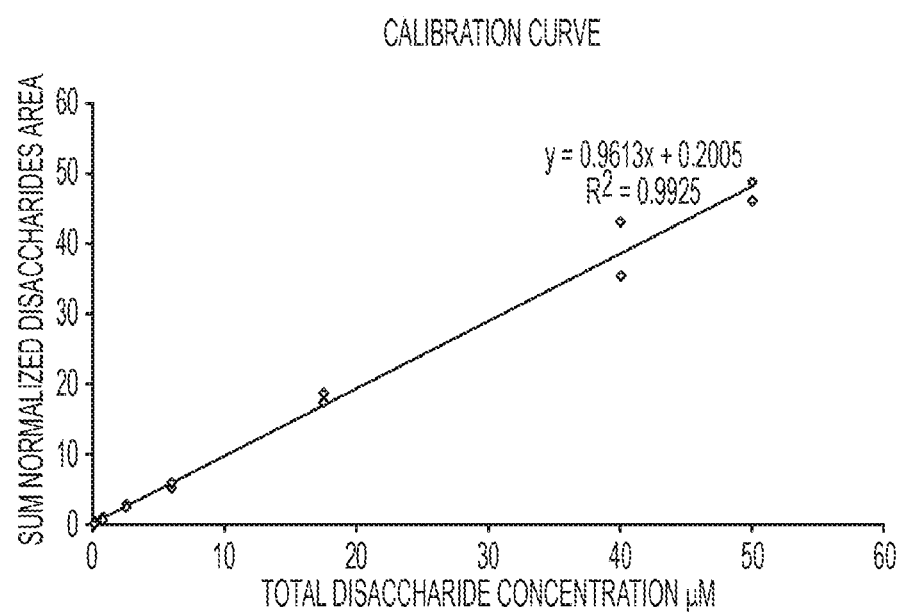
FIG. 5 is an exemplary graph depicting intra-day disaccharide calibration curve linearity and accuracy. To construct the calibration curve, a mixture with a defined ratio of six disaccharides was prepared and spiked into the matrix to be labeled. Eight non-zero standard (STD) concentration levels of the mixture in the range of 0.1 µM to 50.0 µM were used in duplicate. STD1 represents the LLOQ of the assay. A best-fit linear curve was generated to describe the relationship between the nominal concentration of the calibrators and the detector response. The Y-axis represents the summed normalized responses of the six disaccharides to their respective $I_{std}$. The linearity of the relationship was corroborated by a coefficient of determination $R^2=0.99$.

To generate a calibration curve for disaccharide quantification in patient CSF, disaccharide calibrators at different concentrations were spiked in a matrix that mimics that of the patients' samples. To prepare such a matrix, commercial blank CSF was subjected to extraction and desalting. In contrast to patient sample processing, the matrix used in the preparation of the calibrator was not subject to enzymatic digestion. This modification precludes the contribution of low endogenous HS levels to the nominal concentration of spiked-in calibrators. The disaccharide calibrators were added to the prepared matrix after desalting and before labeling, labeled with $^{12}$C-4-NBA and purified by HILIC in the presence of isotopically labeled $I_{std}$. The calibrator was a mixture containing six commercially obtained disaccharides that represent those that are most abundant in the structure of human CSF HS namely, IS, IIS, IIIS, IVS, IIA and IVA. Based on orthogonal methods, the molar ratios were tailored to mimic the approximate disaccharide composition of accumulated HS in CSF of Sanfilippo syndrome A patients. The concentrations used spanned a range where total disaccharide concentrations in patient CSF were expected to fall. The tested range was 0 µM to 50 µM total disaccharides with 0.1 µM being the lower limit of quantification (LLOQ) and 50 µM the upper limit of quantification (ULOQ). The absolute mass spectrometer response of each disaccharide in the calibrator mixture was normalized to that of its respective $^{13}$C $I_{std}$. The sum of the normalized intensities of the six disaccharides was plotted as a function of the total disaccharide concentration in the mixture (FIG. 5). The generated calibration curve was linear with a best-fit equation y=0.9613x+0.2005 and a coefficient of determination ($R^2$) value of 0.99.

To test the accuracy of the best best-fit regression model, the normalized intensity at each calibrator level was back-calculated into a concentration based on the best-fit equation. Accuracy was defined by the deviation of the back-calculated concentration from the theoretical nominal concentration of the calibrator and was reported mathematically as a percent bias (% bias) (Table 2). As shown in Table 2, the bias of the back-calculated mean concentrations ranged from −7% to 12.4%. When the experiment was repeated on different days using freshly prepared calibrators, accuracy at the different levels remained ≤20%.

TABLE 2

Testing of linear regression model for accuracy by back-calculating the normalized detector response at each calibration level to a concentration value using the equation of the linear curve.

| Nominal concentration | STD1 0.100 μM | STD2 0.250 μM | STD3 0.800 μM | STD4 2.50 μM | STD5 6.00 μM | STD6 17.5 μM | STD7 40.0 μM | STD8 50.0 μM |
|---|---|---|---|---|---|---|---|---|
| Mean of back-calculated concentrations | 0.0953 | 0.281 | 0.776 | 2.64 | 5.58 | 18.2 | 39.3 | 47.4 |
| Mean % Bias | −4.7 | 12.4 | −3.0 | 5.6 | −7.0 | 4.0 | −1.8 | −5.2 |
| n | 2 | 2 | 2 | 2 | 2 | 2 | 2 | 2 |

Accuracy and Precision of Quantification Using the Calibration Curve

Quality controls (QC) were samples used to assess the accuracy and precision of a calibration curve-based quantitation. A Disaccharide QC (DS QC) was prepared in a similar fashion to a calibrator using freshly prepared disaccharides mixtures. The DS QC's were quantified based on the calibration curve to assess the accuracy and precision of quantification. Five different QC levels spanning the calibration curve range each in six replicates were used: the LLOQ DS QC (0.1 μM), low DS QC (0.3 μM), low-mid DS QC (2 μM), mid DS QC (15 μM) and high DS QC (37 μM). Table 3 shows the intra-day accuracy and precision data for the quantification of DS QCs. For the LLOQ and low DS QCs the % bias of the mean was respectively 16% and 9% whereas the respective % CVs were to 11.7% and 6.7%. For higher QC levels, accuracy and precision parameters remained ≤20%. This experiment was repeated on three different days and inter-assay accuracy and precision across the five DS QCs levels ranged from −15.7-16% and 2.2-16% respectively.

TABLE 3

Intra-day accuracy and precision of disaccharide quantification using DS QCs.

| | Theoretical nominal concentration | | | | |
|---|---|---|---|---|---|
| | DS QC LLOQ 0.100 μM | DS QC Low 0.300 μM | DS QC Low-Mid 2.00 μM | DS QC Mid 15.0 μM | DS QC High 37.5 μM |
| Intrarun Mean | 0.116 | 0.327 | 2.02 | 14.3 | 35.5 |
| Intrarun % CV | 11.7 | 6.7 | 5.4 | 2.2 | 4.3 |
| Intrarun % Bias | 16 | 9 | 1 | −4.7 | −5.3 |
| n | 6 | 6 | 6 | 6 | 6 |

Recovery

Recovery (R) can be the ratio of amount of product recovered to the initial amount of crude material used in the analytical assay. For the current analytical assay, R was determined by dividing the normalized detector response of a sample where HS was added to the blank non-MPS CSF prior to the initial extraction step to that of another sample where HS was spiked in the same matrix after extraction/desalting and right before digestion. The ratio gauges the amount of material lost during extraction and desalting. For the purpose of this example, the commercial availability of HS from Bovine kidney was relied upon. R was calculated for Low, Low-Mid, Mid and High levels of HS concentrations that, upon digestion, yield a total disaccharide concentration in the quantifiable range of the calibration curve. Interestingly, the recovery values of the assay did not exhibit drastic disparities at the different concentration levels (% CV=13.6) and ranges from 44-58% (Table 4). For the remainder of the examples and where applicable, the average R value between the four HS levels was used.

TABLE 4

| | Recovery | | | |
|---|---|---|---|---|
| | Low HS | Low-Mid HS | Mid HS | High HS |
| Calculated concentration of HS spiked after extraction (μM) | 0.477 | 2.29 | 15.9 | 36.8 |
| Calculated concentration of HS spiked before extraction (μM) | 0.278 | 1.04 | 6.96 | 17.4 |
| R % | 58.3 | 45.4 | 43.8 | 47.3 |

Accuracy and Precision of the Entire Analytical Assay

During the preparation of DS QCs as described above, the disaccharide mixture was spiked in the matrix at the labeling step. Therefore, using such QCs, the accuracy and precision of quantitation was assessed only for part of the assay because variations that take place at the extraction, desalting and digestion steps are not accounted for. Two factors associated with the initial steps of the protocol that can influence the accuracy and precision of the assay are: variability between-sample recovery during extraction and desalting steps and inconsistent enzymatic activity of lyases during enzymatic digestion of HS. To evaluate the combined impact of these factors, heparan sulfate quality controls samples (HS QC) were used. Four different levels of HS QCs were prepared by spiking bovine kidney HS into non-MPS donor CSF at different concentration levels prior the initial anion-exchange extraction step. HS QCs were subjected to the entire sample preparation protocol from extraction to mass spectrometric detection. The disaccharides generated during the process were quantified based on a calibration curve and the value corrected by the average recovery R. The intra-day accuracy of the calculated mean QC concentration fell in the range of −12.8% to 7.9% (Table 5). The range of the intra-day % CVs was 5.0% to 11.4%. Across three different experiments, inter-day accuracy ranged from −12.8% to 7.9% while precision was between 4.6% to 18.3%.

HS QCs were used to test accuracy and precision of the entire analytical assay from the extraction step until the final mass spectrometric detection (Table 5). Low, low-mid, mid and high HS QC levels were used with respective spike-in concentrations of 0.3 μM, 2 μM, 15 μM and 37.5 μM. The quantified level of disaccharide originating from endogenous HS for the CSF lot used in this experiment was 0.407 μM. This value was added to the spike-in concentration to calculate the total nominal concentration.

TABLE 5

Intra-day accuracy and precision of the entire assay using HS QCs.

| | Theoretical nominal concentration + Endogenous | | | |
|---|---|---|---|---|
| | HS QC Low 0.707 µM | HS QC Low-Mid 2.41 µM | HS QC Mid 15.4 µM | HS QC High 37.9 µM |
| Intrarun Mean | 0.656 | 2.45 | 16.4 | 41 |
| Intrarun % CV | 11.3 | 5 | 11.4 | 5.1 |
| Intrarun % Bias | −12.8 | 0 | 5.8 | 7.9 |
| n | 6 | 6 | 6 | 6 |

Reinjection Reproducibility

Reinjection reproducibility determines the amount of previously acceptable calibration standard and quality control value following reinjection. The values were compared against theoretical values (Table 6).

TABLE 6

Analytical QC Summary for Heparan Sulfate Disaccharides (134 hours)

| | DS LLOQ QC 0.1 µM | DS Low QC 0.3 µM | DS Low-Mid QC 2.0 µM | DS Mid QC 15.0 µM | DS High QC 37.5 µM |
|---|---|---|---|---|---|
| Mean | 0.0811 | 0.287 | 1.93 | 14.4 | 35.2 |
| SD | 0.00513 | 0.0124 | 0.0653 | 0.963 | 1.38 |
| % CV | 6.3 | 4.3 | 3.4 | 6.7 | 3.9 |
| % Bias | −18.9 | −4.3 | −3.5 | −4.0 | −6.1 |
| n | 6 | 6 | 6 | 6 | 6 |

Extract Stability

Extract stability of heparan sulfate in processed samples was determined after 192 hours by reinjection of previously acceptable quality control samples that were stored under specified test conditions along with a freshly extracted standard curve and analytical quality control samples (Table 7). The quality control concentrations were calculated from the freshly extracted calibration curve and were compared against theoretical values.

TABLE 7

Extract Stability for Heparan Sulfate (192 hours)

| | LOW QC (HS CSF) ENDOG + 0.3 µM | MID QC (HS CSF) ENDOG + 15.0 µM | HIGH QC (HS CSF) ENDOG + 37.5 µM |
|---|---|---|---|
| Intrarun Mean | 0.601 | 13.8 | 32.8 |
| Intrarun SD | 0.0183 | 1.22 | 3.43 |
| Intrarun % CV | 3.0 | 8.8 | 10.5 |
| Intrarun % Bias | −14.5 | −10.4 | −13.5 |
| N | 6 | 6 | 6 |

Matrix Stability

To evaluate freeze-thaw stability, following an initial freezing period of at least 24 hours, each freeze-thaw cycle included frozen storage for at least 12 hours (Table 8). Matrix stability quality control samples were thawed and maintained per the method conditions that used for study samples. The time interval for each thaw cycle was at least 30 minutes.

TABLE 8

Freeze-Thaw Stability for Heparan Sulfate (5 cycles)

| | Low QC (HS CSF) ENDOG + 0.3 µM | High QC (HS CSF) ENDOG + 37.5 µM |
|---|---|---|
| Intrarun Mean | 0.642 | 36.3 |
| Intrarun SD | 0.0330 | 4.01 |
| Intrarun % CV | 5.1 | 11.0 |
| Intrarun % Bias | 2.9 | −4.0 |
| n | 6 | 6 |

To evaluate bench top stability, matrix stability quality control samples were subjected to conditions relevant to the experimental thawing and aliquotting of study samples (Table 9).

TABLE 9

Bench-Top Stability of Heparan Sulfate in Matrix (23 hours)

| | Low QC (HS CSF) ENDOG + 0.3 µM | High QC (HS CSF) ENDOG + 37.5 µM |
|---|---|---|
| Intrarun Mean | 0.664 | 37.9 |
| Intrarun SD | 0.0407 | 0.88 |
| Intrarun % CV | 6.1 | 2.3 |
| Intrarun % Bias | 6.4 | 0.3 |
| N | 6 | 6 |

Intermediate-term stability was demonstrated during the course of the validation by on-going analysis of quality control samples against freshly prepared curves. The duration of stability was calculated from the time of quality control preparation to completion of extraction of the last accuracy and precision run (not to exceed five weeks) (Table 10).

TABLE 10

Quality Control Samples for Heparan Sulfate in Human Cerebrospinal Fluid

| | HS CSF LOW QC ENDOG + 0.3 µM | HS CSF LOW-MID QC ENDOG + 2.0 µM | HS CSF MID QC ENDOG + 15.0 µM | HS CSF HIGH QC ENDOG + 37.5 µM |
|---|---|---|---|---|
| 1st run | | | | |
| Intrarun Mean | 0.656 | 2.45 | 16.4 | 41.0 |
| Intrarun SD | 0.0743 | 0.122 | 1.87 | 2.08 |
| Intrarun % CV | 11.3 | 5.0 | 11.4 | 5.1 |
| Intrarun % Bias | −12.8 | 0.0 | 5.8 | 7.9 |
| n | 6 | 6 | 6 | 6 |
| 2nd run | | | | |
| Intrarun Mean | 0.624 | 2.27 | 16.3 | 40.0 |
| Intrarun SD | 0.114 | 0.244 | 1.67 | 1.84 |
| Intrarun % CV | 18.3 | 10.7 | 10.2 | 4.6 |
| Intrarun % Bias | −6.4 | −4.2 | 5.8 | 5.5 |
| n | 6 | 6 | 6 | 6 |
| 3rd run | | | | |
| Intrarun Mean | 0.677 | 2.42 | 15.8 | 38.1 |
| Intrarun SD | 0.0417 | 0.215 | 1.39 | 3.90 |
| Intrarun % CV | 6.2 | 8.9 | 8.8 | 10.2 |
| Intrarun % Bias | −3.7 | 0.8 | 2.6 | 0.5 |
| n | 6 | 6 | 6 | 6 |

Solution Stability

The solution stability was demonstrated by comparing the response obtained from a solution stored under the test conditions (e.g., temperature, light exposure, etc.) to the response obtained from an aliquot of the same solution (control) that was not subjected to the test conditions. Long-term solution stability was determined by comparing the response obtained from freshly prepared solutions (control) to the response obtained from a solution maintained at test conditions (e.g., reduced temperature, protected from light). Bench-top solution stability for disaccharides labeled with $^{13}C_6$-4-Butylaniline over a 25 hour period was acceptable with a 1.6% difference between the control and test solution. Bench-top stability for a heparan sulfate stock solution over a 25 hour period was acceptable with a 1.9% difference between the test and control solution. Bench top working solution stability for a disaccharide solution over a 21 hour period was acceptable with a 0.3% difference between the test and control solution. Long term stock solution stability (27 days) for heparan sulfate was acceptable with a 2.0% difference between the test and control solution. Long term stock solution stability for heparan sulfate disaccharides (56-81 days) was acceptable for I-S with a with a 3.0% difference between the test and control solution; for II-S with a 11.5% difference between the test and control solution; IV-S with a −2.9% difference between the test and control solution; IV-A with a 8.8% difference between the test and control solution. Long term stock solution stability for heparan sulfate disaccharide III-S (81 days) was acceptable with a with a −2.4% difference between the test and control solution. Long term working solution stability (56 days) for heparan sulfate disaccharides at a high concentration (50.0 µM) was acceptable with a −1.5% difference between test and control solution.

Conclusions

These data provide a novel, 96 well plate, LC/MS platform for the separation and quantitation of disaccharides generated by enzymatic digestion of HS. Powerful chromatographic methods have been previously utilized for HS disaccharide analysis such as strong anion exchange (SAX). Although effective, many prior chromatographic methods can face technical challenges. The high content of non-volatile salts used during SAX separations can preclude their direct coupling with mass spectrometers without special online desalting devices. IPRP chromatography can require long, time-consuming gradients and can rely on the use of millimolar concentration of alkyl ammonium salts in its mobile phases at the risk of contaminating mass spectrometric detectors. This can often require the dedication of the instrument in operation to one application. PGC can retain the different HS disaccharides differentially with highly sulfated difficult to elute causing their loss (Gill, V. L. et al., Anal. Chem. (2013) 85(2):1138-1145). HILIC can require long separation times (>30 minutes) to achieve optimal separation at the expense of throughput. The current method circumvents many or all of these challenges in part, and in certain instances, by using common mass spectrometry friendly buffers such as ammonium acetate while retaining resolving power. The method is capable of offering a relatively rapid 12 minutes LC/MS method and throughput.

The present Example includes the use of a labeling approach in which internal standards are generated for selected analytes by using an isotopically labelled version of a labeling agent. The presently exemplified methods can also be advantageous in that they incorporate an $I_{std}$. Such an $I_{std}$ addresses the difficulty of identifying a single molecule to mimic the behavior of all HS disaccharides and/or cleavage products.

The use of purified disaccharides in the construction of the calibration curve provides a reliable source of standards and enables tailoring of the calibrator mixture to a composition that mirrors that of a relevant human CSF HS sample for accurate quantification.

Figure 6:
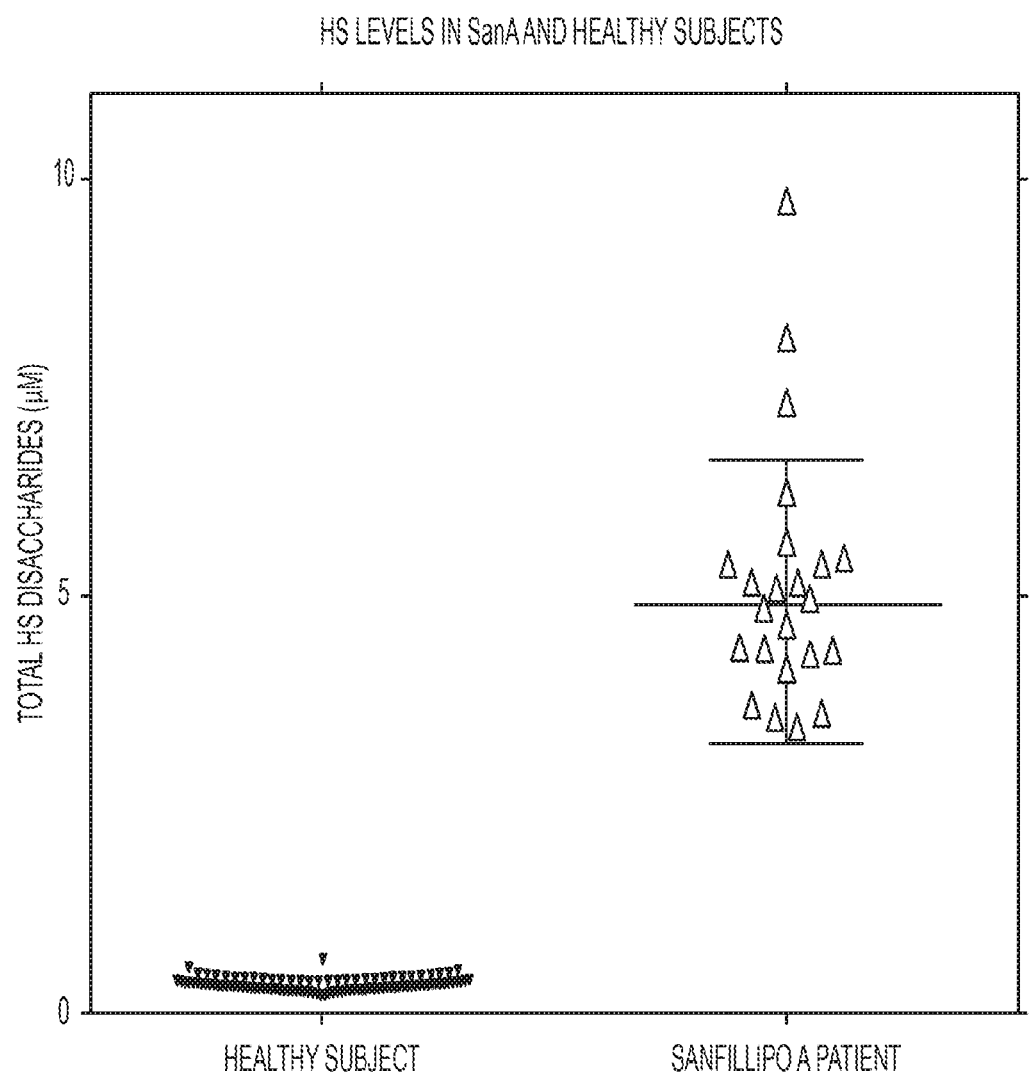
FIG. 6 is an exemplary graph depicting HS levels in the CSF of Sanfilippo syndrome A patients versus controls. Control samples with HS concentrations below the lower limit of quantification (n=53) were not plotted.

Example 2: Cerebrospinal Fluid Heparan Sulfate Concentration in Untreated Sanfilippo Syndrome A Patients CSF samples from 25 untreated Sanfilippo syndrome A patients were analyzed using the LC/MS-based HS assay described above. The HS concentrations were compared to those of 156 control, healthy individuals whose CSF was obtained from a biorepository and analyzed using the same method. In the patient group, HS concentrations ranged from 1.94 µM to 9.71 µM with a mean HS concentration of 4.9 µM (FIG. 6). In contrast, 33% of the control samples are characterized by HS levels below the lower limit of quantification (LLOQ) of the assay. Those in the quantifiable range had a mean concentration of 0.37 µM with the lowest and highest and concentrations being 0.229 µM and 0.648 µM respectively. Therefore, there is a significant, 13-fold increase (t-test; P<0.001) in HS levels in the CSF of Sanfilippo syndrome Type A patients as compared to control subjects.

Figure 7:
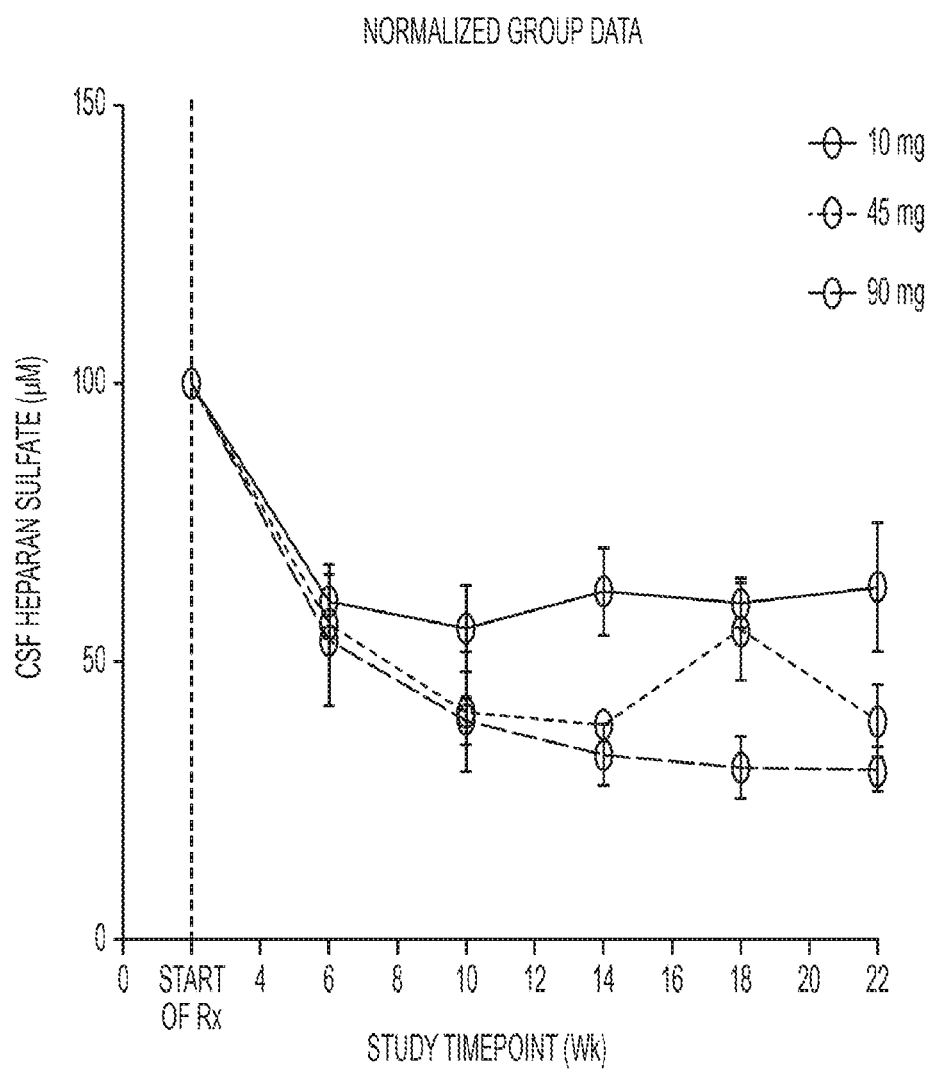
FIG. 7 is an exemplary graph depicting the change in HS concentration in CSF following intrathecal administration of recombinant heparan N-sulfatase enzyme replacement therapy in Sanfilippo syndrome A patients.

Example 3: Change in HS Concentration after Intrathecal Enzyme Replacement Therapy in Sanfilippo Syndrome A Patients The present Example relates, in part, to the application of a method of the present invention to the monitoring of patient status and treatment efficacy. Patients with Sanfilippo syndrome A were administered 10 mg, 45 mg or 90 mg of recombinant heparan N-sulfatase monthly by intrathecal administration for a period of 22 weeks. A CSF sample was collected prior to each dose of recombinant heparan N-sulfatase and the HS in the CSF was measured using the LC/MS-based HS assay described above. The change in CSF HS over the 22 week treatment period is shown in FIG. 7. At all dosage amounts, the concentration of HS in the CSF sample decreased by 50% relative to baseline (i.e., the sample collected prior to the first treatment dose). These data demonstrate, among other things, that CSF HS levels remained stable during the treatment course and that the lowest levels of CSF HS were achieved at the 90 mg dose.

Figure 8:
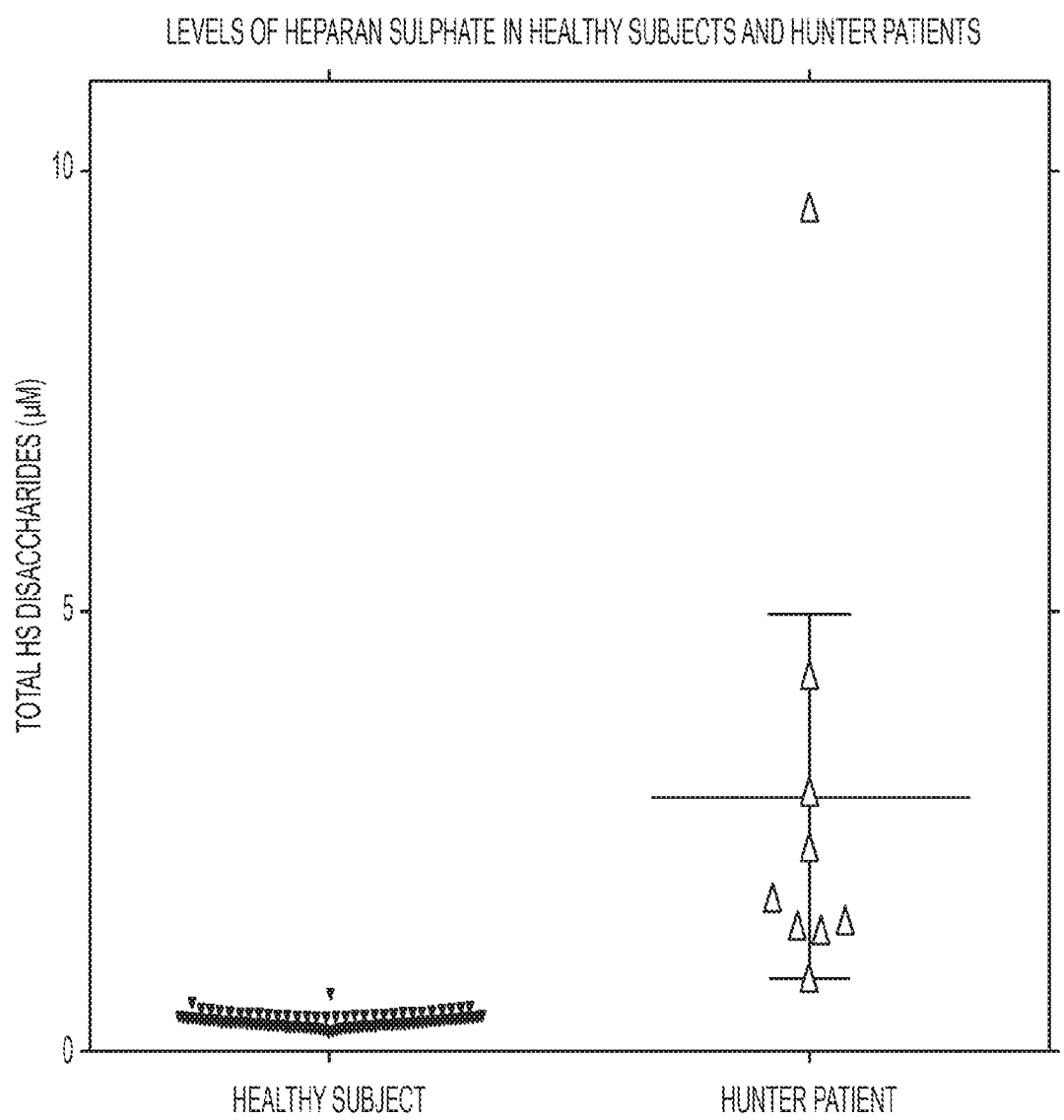
FIG. 8 is an exemplary graph depicting HS levels in the CSF of Hunter syndrome patients versus controls. Controls samples with HS concentrations below the lower limit of quantification (n=53) were not plotted.

Example 4: Cerebrospinal Fluid Heparan Sulfate Concentration in Untreated Hunter Syndrome Patients CSF samples from 9 untreated Hunter syndrome patients were analyzed using the LC/MS-based HS assay described in Example 1. The HS concentrations were compared to those of 156 control, healthy individuals whose CSF was obtained from a biorepository and analyzed using the same method. In the patient group, HS concentrations ranged from 0.8 µM to 9.5 µM with a mean HS concentration of 2.9 µM (FIG. 8). In contrast, 33% of the control samples were characterized by HS levels below the lower limit of quantification (LLOQ) of the assay. Those in the quantifiable range had a mean concentration of 0.37 µM, with the lowest and highest and concentrations being 0.229 µM and 0.648 µM respectively. Therefore, there was a significant, 7.8-fold increase (t-test; P<0.001) in HS levels in the CSF of Hunter syndrome patients as compared to control subjects.

Example 5: Collection and Analysis of Cerebrospinal Fluid in Pediatric and Adult Patients with Hunter Syndrome Patients Adult patients aged ≥18 years and pediatric patients aged <18 years with a documented diagnosis of MPS II were enrolled. All patients were being treated with intravenous idursulfase ERT. Pediatric patients were eligible to participate only if they had been scheduled prior to screening to undergo a nonstudy-related lumbar puncture (LP) or other medical or diagnostic procedure requiring administration of general anesthesia. Adult patients could voluntarily opt to undertake LP. Adult patients were required to have an intelligence quotient of ≥78 determined through cognitive assessment at, or within 3 months prior to, screening/baseline. No formal cognitive testing was required for pediatric patients.

Patients were excluded at screening who had a history of complications from previous LPs, or technical challenges in performing one; had received an hematopoietic stem cell transplant; had taken aspirin, nonsteroidal anti-inflammatory drugs, or other medications that could affect blood clot formation within the 7 days prior to LP, or had ingested such medications within 7 days prior to any study-related procedure in which a change in potential blood clot formation would be deleterious.

Study Design

The planned duration of a patient's participation was approximately 3 weeks: consisting of a 2-week screening/baseline period, approximately 1 day for laboratory and cognitive assessments, and 1 day for CSF collection (via LP or other previously scheduled procedure allowing access to CSF such as intracranial pressure monitoring device insertion (pressure bolt procedure), or during cervical spinal cord decompression procedure). A follow-up for safety evaluation was conducted by telephone approximately 1 week post CSF collection (Day 8).

Screening/baseline procedures included physical examination, medical history and vital signs for all patients. Baseline serum chemistry, hematology, and urinalysis were also performed only for adult patients undergoing elective LP. Adult patients also underwent cognitive evaluation by a certified psychologist or by qualified staff under the supervision of a licensed psychologist, using the Wechsler Adult Intelligence Scale-Fourth Edition (WAIS-IV) (Wechsler, D. (2008) Wechsler Adult Intelligence Scale. 4 ed. San Antonio, Tex.: The Psychological Corporation). Although cognitive evaluation of pediatric patients was not required, investigators recorded their opinion about the patient's cognitive status. For pediatric patients unable to complete screening/baseline procedures because of their previously scheduled, nonstudy-related procedure, medical history and safety data were collected by review of medical charts. Patients given LP were monitored for at least 2 hours post procedure before being discharged.

Outcome and Safety Measures

The primary outcome measure was the total GAG concentration in the CSF. Safety measures consisted of documentation of adverse events (AEs).

Pharmacodynamic/Biomarker Analysis

The level of total HS in CSF was determined by liquid chromatography-tandem mass spectrometry (LC-MS/MS). Briefly, HS in the CSF was first extracted using an anion-exchange resin and then digested by a combination of enzymes including heparinase I, II, and III. The resultant HS disaccharides were labeled with $^{12}$C-4-N-butylaniline by reductive amination and then analyzed by LC-MS/MS. The level of total CSF HS was derived from the combined signal intensity of the 6 most abundant (referring to their signal intensities) disaccharides using purified bovine HS as the positive control.

Patient Disposition

Figure 9:
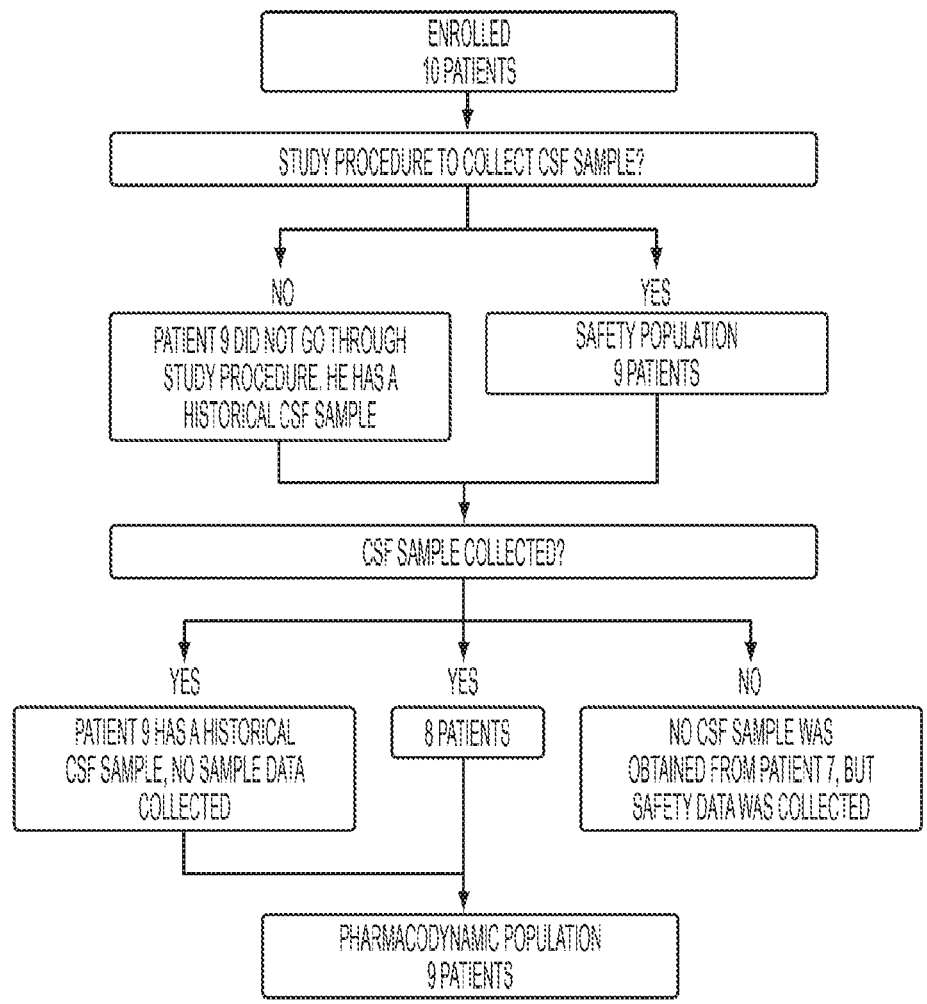
FIG. 9 is an exemplary diagram depicting disposition of enrolled study patients.

Ten patients met the study inclusion criteria and were enrolled in the study at 7 centers, 5 in the United States and 2 in the United Kingdom (FIG. 9). All 10 enrolled patients completed the study. Of these patients, 8 had evaluable CSF samples and were included in both the safety and pharmacodynamic populations. Of the remaining 2 patients, one patient had an unsuccessful LP and the second consented to provide a retrospective CSF sample for GAG analysis. The first patient with the unsuccessful LP was evaluated as part of the safety population, but not of the pharmacodynamics population, and the second one was part of the pharmacodynamics population, but not of the safety evaluation. Thus, both the safety and pharmacodynamics populations each had 9 patients, with 8 of them overlapping.

Patient Characteristics

Patient baseline demographic and clinical characteristics are shown in Table 11. The study population included 5 adults patients aged >18 years and 5 pediatric patients aged <18 years. The mean age overall at baseline (CSF and urine sample collection) was 17.9 years (range 4.1-36.8 years. Among the 5 adults, mean age was 27.9 years and among the 5 pediatric patients mean age was 7.8 years. Scores of the WAIS-IV, administered to the adult patients only, ranged from 88-111 with a mean score of 99.6. Cognitive status among the pediatric patients, recorded as either normal or abnormal, was abnormal in 3 patients and normal in 2 patients.

TABLE 11

Patient baseline characteristics and CSF/uGAG results.

| | Age (y) at: | | | | | | CSF | | |
|---|---|---|---|---|---|---|---|---|---|
| Patient | Onset MPS II Symptoms | MPS II Diagnosis | CSF/Urine Sample Collection | Height (cm) | Weight (kg) | Cognitive Assessment (Method) | CSF GAG (ng/mL) | Non-DS (ng/mL) | CSF HS (μM) |
| 1. | 3.0 | 4.2 | 8.0 | 127.6 | 23.9 | Normal[a] | 373.4 | <36.7[b] | 1.74 |
| 2. | 4.0 | 5.8 | 16.2 | 148.4 | 67.2 | Normal[a] | 356.8 | <36.7[b] | 0.80 |
| 3. | n/k | 4.8 | 21.4 | 160.4 | 61.6 | 88 (WAIS-IV)[c] | 459.3 | <36.7[b] | 1.42 |
| 4. | 0.8 | 1.4 | 25.4 | 137.0 | 56.8 | 93 (WAIS-IV)[c] | 455.2 | 61.2 | 9.57 |
| 5. | 3.0 | 3.9 | 26.5 | 152.5 | 63.2 | 105 (WAIS-IV)[c] | 1,181.1 | <36.7[b] | 1.48 |

TABLE 11-continued

Patient baseline characteristics and CSF/uGAG results.

| | Age (y) at: | | | | | | CSF | | |
|---|---|---|---|---|---|---|---|---|---|
| Patient | Onset MPS II Symptoms | MPS II Diagnosis | CSF/Urine Sample Collection | Height (cm) | Weight (kg) | Cognitive Assessment (Method) | CSF GAG (ng/mL) | Non-DS (ng/mL) | CSF HS (μM) |
| 6. | 6.9 | 6.9 | 29.5 | 131.2 | 57.2 | 101 (WAIS-IV)$^c$ | 381.5 | <36.7$^b$ | 1.38 |
| 7.$^e$ | n/k | 3.5 | 36.8 | 166.9 | 87.4 | 111 (WAIS-IV)$^c$ | — | — | — |
| Median (range) | 3 (0.8-6.9) | 3.7 (1.3-6.9) | 18.8 (4.1-36.8) | 134.1 (110.0-166.9) | 57.0 (23.0-87.4) | — | 418.4 (356.8-1181.1) | <36.7$^b$ (<36.7-63.1) | 1.45 (0.80-9.57) |
| 8. | 1.0 | 1.3 | 4.1 | 114.0 | 23.0 | Abnormal$^e$ | 842.9 | <36.7$^b$ | 2.94 |
| 9.$^f$ | n/k | 3.3 | 4.6 | 110.0 | 23.8 | Abnormal$^e$ | 2,360.9 | 63.1 | 4.26 |
| 10. | 1.0 | 3.5 | 6.3 | 120.0 | 30.8 | Abnormal$^e$ | 939.7 | <36.7$^b$ | 2.32 |
| Median (range) | 2.8 | 3.9 | 17.9 | 136.8 | 49.5 | — | 939.7 (842.9-2360.9) | <36.7$^b$ | 2.94 (2.32-4.26) |

$^a$Cognitive status of all pediatric patients (aged <18 years) was determined by investigator opinion;
$^b$Lower limit of quantitation;
$^c$Per study eligibility criteria, adult patients (aged ≥18 years) were required to have an IQ ≥78;
$^d$Patient underwent 2 lumbar puncture procedures, the second of which was successful, and had 2 urine samples collected with GAG measured in each;
$^e$Patient evaluable for safety assessment only;
$^f$Patient evaluable for pharmacodynamic assessment only;
n/k, not known;
WAIS-IV, Wechsler Adult Intelligence Scale.

All 9 patients included in the safety population were receiving intravenous idursulfase. Other commonly used medications by therapeutic class (≥3 [33%] patients) included anilides and natural opium alkaloids, serotonin antagonists, amides, benzodiazepine derivatives, melatonin receptor agonists, and other general anesthetics. The commonly used medications reflected the surgical/medical treatment profile of the population.

GAG Analysis

All 5 adult patients underwent an LP, although the CSF collection was unsuccessful in 1 of these patients, who was included in the safety population only; another patient required 2 LPs, the second of which was successful (Table 11). Among the 9 patients, including all 5 children with CSF samples (pharmacodynamic population), the volume of CSF collected per patient ranged from 1.5-16.0 mL. Total GAG concentrations ranged from 356.8-2,360.9 ng/mL. Among the children only, CSF total GAG concentrations ranged from 356.8-2,360.9 ng/mL. For the adults only, GAG concentration were 381.5-1,181.1 ng/mL.

Figure 10:
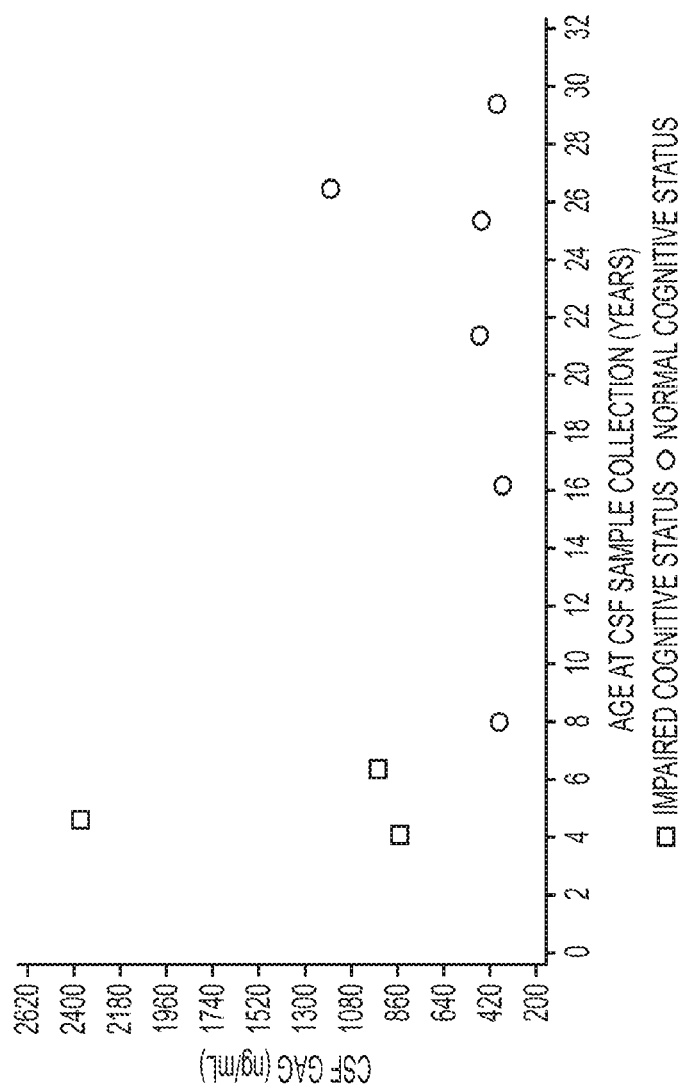
FIG. 10 is an exemplary graph depicting CSF GAG concentrations by age and cognitive status (pharmacodynamic population). Values less than the lower limit of quantitation (LLOQ) were replaced with the LLOQ value.

The 3 cognitively impaired children had CSF GAG levels of 842.9 ng/mL, 939.7 ng/mL, and 2,360.9 ng/mL, compared with a range of 356.8-1181.1 ng/mL in 6 of the remaining patients with normal cognition (4 adults and 2 children). FIG. 10 provides a scatter plot of these CSF GAG levels by age at CSF collection and baseline cognitive status. Some correlation between cognitive assessment score and total CSF GAG level was observed.

Non-DS GAG CSF levels were below the lower limit of quantitation (36.7 ng/mL) in 7 of 9 patients; in the 2 other patients the non-DS GAG CSF level was 61.2 ng/mL in an adult and 63.1 ng/mL in a child. This suggests that DS is the major component in CSF GAG of both adult and pediatric patients with MPS II.

Levels of CSF HS were determined by mass spectroscopy. The levels of HS were quantifiable in all analyzed samples. All patients had levels above the normal range, which preliminary data indicates is around 0.4-0.5 μM. The cognitively intact patients had, in general, lower HS values (5 out of 6 patients had levels 0.2-1.5 μM) than the cognitively impaired patients (2.3-4.3 μM); the highest recorded value (9.57 μM) was in a cognitively intact adult patient.

Conclusions

These data demonstrate that patients with normal cognitive development/attenuated MPS II generally may have lower CSF GAG levels than those with the severe phenotype. Of the 6 patients (adult and pediatric) whose cognitive status was rated as normal, 5 had CSF GAG values in the range of 360 ng/mL to 460 ng/mL, while the GAG value from the remaining patient was 1181.1 ng/mL. In contrast, all 3 pediatric patients with abnormal cognition had values >840 ng/mL. The levels of HS, as measured by mass spectroscopy, generally followed a similar pattern, with all MPS II patients having abnormally high values compared to healthy subjects, and with the patients with the severe phenotype having the highest values. However, the highest HS value was observed in a cognitively intact adult (but who was not the same subject as the cognitively intact adult with the highest total CSF GAG value).

Biochemical means of predicting MPS II phenotype as early as possible is a valuable asset for optimal patient management. Predicting whether a child with MPS II will develop cognitive impairment can be a difficult task for the clinician (Martin, R. et al., Pediatrics (2008) 121(2):e377-386; Burton, B. K. et al., Eur. J. Pediatr. (2012) 171(4):631-639; Scarpa, M. et al., Orphanet J. Rare Dis. (2011)6(1):72). Genetic mutational analysis is often of limited value, (Martin, R. et al., Pediatrics (2008) 121(2):e377-386) and although from the clinical perspective, some early signs predictive of neurological involvement have been identified, including sleep disturbance, increased activity, behavior problems, seizure-like behavior, perseverative chewing, and unsuccessful bowel and bladder training, (Holt, J. et al., J. Pediatr. (2011)159(2):320-326) their usefulness is limited by their lack of specificity. Similarly, although brain imaging has identified higher rates of brain atrophy, hydrocephalus, and severe white matter lesions in cognitively impaired versus cognitively intact patients, these indicators were not diagnostic of the severe phenotype because they also occurred in some patients without cognitive impairment (Muenzer, J. et al., Pediatrics (2009)124(6):e1228-e1239;

Vedolin, L. et al., Neurology (2007)69(9):917-924). Thus, in the absence of a family history of MPS II, and when faced with a novel or very rare mutation, the clinician often employs a wait-and-see approach, with close monitoring of cognitive development.

The present data indicate that clinicians may be able to identify MPS II with neurological involvement biochemically, by measuring CSF GAG levels. Analysis of GAG levels in the CSF and urine in patients with MPS II indicated that the levels were higher in pediatric patients with abnormal cognition, compared with cognitively intact adults and pediatric patients.

Example 6: Treatment of Sanfilippo Syndrome A Patients with Recombinant Human N-Sulfatase This Example relates, in general, among other things, to the use of a mass spectrometry assay for HS in the evaluation and/or monitoring of a therapeutic treatment. This Example describes a multicenter, multiple-dose, dose escalation study designed to evaluate the safety, tolerability and clinical activity of up to three dose levels of recombinant human heparan N-sulfatase (rhHNS) administered intrathecally to patients with MPS IIIA (i.e., Sanfilippo syndrome A). Patients with Sanfilippo syndrome A were treated with 10 mg, 45 mg, or 90 mg of rhHNS once every 4 weeks. Patients had not been previously treated by drug or device for Sanfilippo syndrome A, although those patients who entered the extension study had received 5 or 6 scheduled doses of rhHNS in the prior study. The duration of the treatment was 6 months, and for those patients who entered the extension study, the duration of treatment was 48 months.

Inclusion criteria included a documented deficiency in sulfamidase enzyme activity of less than or equal to 10% of the lower limit of the normal range as measured in fibroblast or leukocytes and either, a) a normal enzyme activity level of at least one other sulfatase (to rule out multiple sulfatase deficiency) as measured in fibroblast or leukocytes or, b) two documented mutations. In order to enter the study, patients also had to be 3 years of age or older with a developmental age of 1 year or older. Patients also had to be medically stable.

Patients were excluded from the study if they had significant non-MPS IIIA related CNS impairment or behavior disturbances that would confound the scientific integrity or interpretation of study assessments. Patients were also excluded if they had received a hematopoietic stem cell or bone marrow transplant or had been treated with any investigational drug or device intended to treat MPS IIIA within 30 days prior to enrollment in the study.

The clinical assessments evaluated in the study included measuring (1) change from the baseline values, and (2) comparison of values obtained in a longitudinal, 24 month, natural history study of untreated MPS IIIA patients. Clinical assessments included concentration of rhHNS in CSF and serum, concentration of safety and potential surrogate efficacy biomarkers in CSF, urine and serum, concentration of heparan sulfate and heparan sulfate derivatives in urine and CSF as measured over approximately 6 months. Additional assessments included standardized neurocognitive and behavioral assessments, Sanfilippo-specific behavioral rating scales, gross and fine motor assessments, functional adaptive rating scales, quality of life questionnaires, and Children's Sleep Habits Rating Scale, brain MRI and ABR.

Heparan Sulfate Levels

Heparan sulfate is a primary accumulating metabolite in MPS IIIA and a key pharmacodynamics endpoint indicating in vivo activity of the rhHNS in the central nervous system. The level of the glycosaminoglycan (GAG) heparan sulfate in CSF over the duration of the study was measured. Total urinary GAG was also assessed.

The level of total heparan sulfate in CSF was measured in a validated LC-MS based assay, as described above in Example 1, and based on six abundant HS-derived disaccharides after enzymatic HS digestion. The disaccharides were quantified based on a calibration curve generated using six commercially obtained disaccharide standards that are abundant in human CSF HS.

Figure 11:
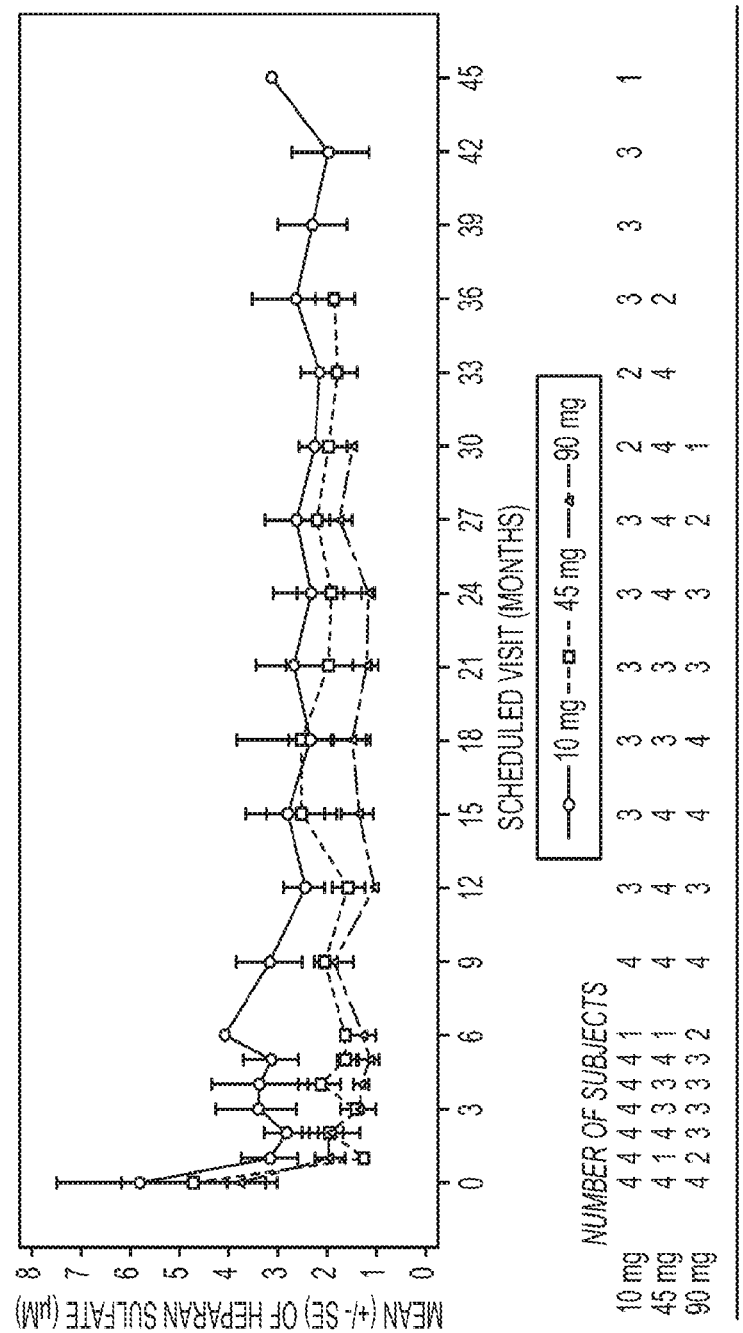
FIG. 11 is an exemplary graph depicting CSF GAG concentrations in Sanfilippo syndrome A patients treated with recombinant human heparan N-sulfatase.

Over the course of the study, the mean CSF total heparan sulfate levels were reduced at each of the three dose levels as compared to baseline (i.e., prior to the first treatment dose) (FIG. 11). The declines were evident following the first dose of intrathecal rhHNS (i.e., observed four weeks following the first dose and immediately prior to the second dose). The 45 mg and 90 mg doses reduced total heparan sulfate levels in the CSF in a similar manner and to a greater extent than the 10 mg dose. Over the course of the study, from 24 to 45 months, the declines in CSF heparin sulfate appear to be sustained.

These data indicate that CSF total heparan sulfate exhibited declines in response to therapy at all dose levels, with a greater impact observed at the higher dose levels. Most of the reduction occurred after the first dose (week 6) with levels remaining relatively stable during the remainder of the treatment period. An effect on CSF heparan sulfate may contribute to the therapeutic benefit of rhHNS and demonstrates that rhHNS administered intrathecally exhibits biological activity.

Other Embodiments

While a number of embodiments of this invention are described herein, the present disclosure and examples may be altered to provide other methods and compositions of this invention. Therefore, it will be appreciated that the scope of this invention is to be defined by the appended claims in addition to the specific embodiments that have been represented by way of example. All references cited herein are hereby incorporated by reference.

What is claimed is:

1. A method of determining glycosaminoglycan (GAG) level in a biological sample, the method comprising the steps of:
   a) incubating a biological sample with one or more enzymes under conditions that permit digestion of glycosaminoglycan to generate a mixture of disaccharides;
   b) chemically derivatizing the mixture of disaccharides generated in step a);
   c) measuring an amount of each individual derivatized disaccharide;
   d) determining the glycosaminoglycan (GAG) level in the biological sample based on the amount of each individual derivatized disaccharide measured at step c), wherein the step c) comprises
   (i) separating individual derivatized disaccharides by chromatography; and
   (ii) measuring each individual derivatized disaccharide by mass spectrometry, and wherein the amount of each individual derivatized disaccharide is measured as compared with an internal standard, and wherein each individual disaccharide is derivatized with 4-Butylaniline and the internal standard for each corresponding disaccharide is labeled with $^{13}C_6$-4-Butylaniline.

2. The method of claim 1, wherein the glycosaminoglycan comprises heparan sulfate.

3. The method of claim 1, wherein the one or more enzymes comprise one or more heparinases.

4. The method of claim 3, wherein the one or more heparinases comprises heparinases I, II and/or III.

5. The method of claim 1, wherein the one or more enzymes comprise one or more enzymes selected from the group consisting of chondroitinase AC, chondroitinase B, chondroitinase C, Chondroitinase ABC and keratanases.

6. The method of claim 1, wherein the mixture of disaccharides comprises disaccharides I-S (ΔUA,2S-GlcNS,6S), II-S (ΔUA-GlcNS,6S), III-S (ΔUA,2SGlcNS), IV-S (ΔUA-GlcNS), II-A (ΔUA-GlcNAc,6S), and/or IV-A (ΔUA-GlcNAc).

7. The method of claim 6, wherein the measuring comprises measuring the amount of each of derivatized I-S (ΔUA,2S-GlcNS,6S), derivatized II-S (ΔUA-GlcNS,6S), derivatized III-S (ΔUA,2S-GlcNS), derivatized IV-S (ΔUA-GlcNS), derivatized II-A (ΔUA-GlcNAc,6S), and derivatized IV-A (ΔUA-GlcNAc).

8. The method of claim 1, wherein the mixture of disaccharides is derivatized with a hydrophobic moiety.

9. The method of claim 1, wherein the chromatography is reverse-phase liquid chromatography.

10. The method of claim 1, wherein the glycosaminoglycan (GAG) level in the biological sample is determined by summed disaccharide concentration value based on the amount of each individual disaccharide measured.

11. The method of claim 1, wherein the biological sample is a cerebrospinal fluid (CSF) sample, a blood sample, a plasma sample, or a urine sample.

* * * * *